(12) United States Patent
Wang et al.

(10) Patent No.: US 8,660,628 B2
(45) Date of Patent: Feb. 25, 2014

(54) ANALYTE SENSORS COMPRISING BLENDED MEMBRANE COMPOSITIONS AND METHODS FOR MAKING AND USING THEM

(75) Inventors: Jenn-Hann Larry Wang, Northridge, CA (US); Tri T. Dang, Winnetka, CA (US); Brooks B. Cochran, Northridge, CA (US); John J. Mastrototaro, Los Angeles, CA (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 949 days.

(21) Appl. No.: 12/643,790

(22) Filed: Dec. 21, 2009

(65) Prior Publication Data

US 2011/0152654 A1 Jun. 23, 2011

(51) Int. Cl.
*A61B 5/05* (2006.01)

(52) U.S. Cl.
USPC ............................ 600/345; 600/347; 600/365

(58) Field of Classification Search
USPC ........ 600/309, 316, 345–347, 365; 435/4, 14; 436/68; 422/50, 420–429; 204/403.01–403.15; 702/23; 604/64–66
See application file for complete search history.

(56) References Cited

U.S. PATENT DOCUMENTS

| | | | |
|---|---|---|---|
| 2,402,950 A | 7/1946 | Culver et al. | |
| 2,519,541 A | 8/1950 | Bryant | |
| 2,899,658 A | 8/1959 | Bean, Jr. | |
| 4,034,959 A | 7/1977 | Morrison | |
| 4,104,099 A | 8/1978 | Scherrer | |
| 4,136,250 A | 1/1979 | Mueller et al. | |
| 4,163,544 A | 8/1979 | Fowler et al. | |
| 4,356,074 A | 10/1982 | Johnson | |
| 4,373,009 A | 2/1983 | Winn | |
| 4,373,527 A | 2/1983 | Fischell | |
| 4,484,987 A | 11/1984 | Gough | |
| 4,560,375 A | 12/1985 | Schulte et al. | |
| 4,568,250 A | 2/1986 | Falk et al. | |
| 4,569,641 A | 2/1986 | Falk et al. | |
| 4,573,994 A | 3/1986 | Fischell et al. | |
| 4,626,244 A | 12/1986 | Reinicke | |
| 4,636,150 A | 1/1987 | Falk et al. | |
| 4,654,006 A | 3/1987 | Kusano et al. | |
| 4,714,234 A | 12/1987 | Falk et al. | |

(Continued)

FOREIGN PATENT DOCUMENTS

| | | |
|---|---|---|
| EP | 0747069 | 12/1996 |
| EP | 0826382 | 3/1998 |

(Continued)

OTHER PUBLICATIONS

Ianniello et al. Differential pulse voltammetric study of direct electron transfer in glucose oxidase chemically modified graphite electrodes, Anal. Chem., 1982, 54 (7), pp. 1098-1101.*

(Continued)

*Primary Examiner* — Michael D'Angelo
(74) *Attorney, Agent, or Firm* — Gates & Cooper LLP

(57) ABSTRACT

Embodiments of the invention provide analyte sensors having elements designed to modulate their chemical reactions as well as methods for making and using such sensors. In certain embodiments of the invention, the sensor includes an analyte modulating membrane that comprises a blended mixture of a linear polyurethane/polyurea polymer, and a branched acrylate polymer.

16 Claims, 13 Drawing Sheets

(56) References Cited

U.S. PATENT DOCUMENTS

| | | | |
|---|---|---|---|
| 4,759,828 | A | 7/1988 | Young et al. |
| 4,769,013 | A | 9/1988 | Lorenz et al. |
| 4,783,441 | A | 11/1988 | Thurow |
| 4,890,620 | A | 1/1990 | Gough |
| 4,897,173 | A | 1/1990 | Nankai et al. |
| 4,950,256 | A | 8/1990 | Luther et al. |
| 4,958,661 | A | 9/1990 | Holtermann et al. |
| 5,001,009 | A | 3/1991 | Whitbourne |
| 5,019,260 | A | 5/1991 | Gsell et al. |
| 5,077,210 | A | 12/1991 | Eigler et al. |
| 5,108,819 | A | 4/1992 | Heller et al. |
| 5,128,170 | A | 7/1992 | Matsuda et al. |
| 5,165,407 | A | 11/1992 | Wilson et al. |
| 5,178,366 | A | 1/1993 | Kojima et al. |
| 5,183,472 | A | 2/1993 | Jaehrling et al. |
| 5,196,088 | A | 3/1993 | Soda |
| 5,200,051 | A | 4/1993 | Cozzette et al. |
| 5,212,050 | A | 5/1993 | Mier et al. |
| 5,229,172 | A | 7/1993 | Cahalan et al. |
| 5,281,324 | A | 1/1994 | Kiesele et al. |
| 5,288,636 | A | 2/1994 | Pollmann et al. |
| 5,299,571 | A | 4/1994 | Mastrototaro |
| 5,322,063 | A | 6/1994 | Allen et al. |
| 5,328,954 | A | 7/1994 | Sarangapani |
| 5,330,911 | A | 7/1994 | Hubbell et al. |
| 5,331,027 | A | 7/1994 | Whitbourne |
| 5,390,671 | A | 2/1995 | Lord et al. |
| 5,390,691 | A | 2/1995 | Sproule |
| 5,391,250 | A | 2/1995 | Cheney, II et al. |
| 5,411,647 | A | 5/1995 | Johnson et al. |
| 5,415,938 | A | 5/1995 | Cahalan et al. |
| 5,433,710 | A | 7/1995 | Van Antwerp et al. |
| 5,482,473 | A | 1/1996 | Lord et al. |
| 5,568,806 | A | 10/1996 | Cheney, II et al. |
| 5,607,475 | A | 3/1997 | Cahalan et al. |
| 5,609,629 | A | 3/1997 | Fearnot et al. |
| 5,620,738 | A | 4/1997 | Fan et al. |
| 5,643,681 | A | 7/1997 | Voorhees et al. |
| 5,648,442 | A | 7/1997 | Bowers et al. |
| 5,662,960 | A | 9/1997 | Hostettler et al. |
| 5,672,638 | A | 9/1997 | Verhoeven et al. |
| 5,696,314 | A | 12/1997 | McCaffrey et al. |
| 5,702,754 | A | 12/1997 | Zhong |
| 5,702,818 | A | 12/1997 | Cahalan et al. |
| 5,711,959 | A | 1/1998 | Kohler et al. |
| 5,777,060 | A | 7/1998 | Van Antwerp |
| 5,786,439 | A | 7/1998 | Van Antwerp et al. |
| 5,804,048 | A | 9/1998 | Wong et al. |
| 5,809,242 | A | 9/1998 | Shaw et al. |
| 5,858,186 | A | 1/1999 | Glass |
| 5,913,040 | A | 6/1999 | Rakavy et al. |
| 5,939,208 | A | 8/1999 | Stoy |
| 5,964,993 | A | 10/1999 | Blubaugh, Jr. et al. |
| 6,011,537 | A | 1/2000 | Slotznick |
| 6,013,855 | A | 1/2000 | McPherson et al. |
| 6,030,827 | A | 2/2000 | Davis et al. |
| 6,103,033 | A | 8/2000 | Say et al. |
| 6,134,461 | A * | 10/2000 | Say et al. ....................... 600/345 |
| 6,162,611 | A | 12/2000 | Heller et al. |
| 6,340,421 | B1 | 1/2002 | Vachon et al. |
| 6,368,274 | B1 | 4/2002 | Van Antwerp et al. |
| 6,411,998 | B1 | 6/2002 | Bryant et al. |
| 6,413,393 | B1 | 7/2002 | Van Antwerp et al. |
| 6,497,729 | B1 | 12/2002 | Moussy et al. |
| 6,551,276 | B1 | 4/2003 | Mann et al. |
| 6,558,351 | B1 | 5/2003 | Steil et al. |
| 6,741,877 | B1 | 5/2004 | Shults et al. |
| 7,613,491 | B2 | 11/2009 | Boock et al. |
| 2003/0100040 | A1 | 5/2003 | Bonnecaze et al. |
| 2004/0008956 | A1 | 1/2004 | Frohne et al. |
| 2004/0009161 | A1 | 1/2004 | Escary |
| 2004/0074785 | A1 | 4/2004 | Holker et al. |
| 2004/0090607 | A1 | 5/2004 | Yoshida |
| 2005/0090607 | A1 | 4/2005 | Tapsak et al. |
| 2005/0272989 | A1 | 12/2005 | Shah et al. |
| 2006/0052745 | A1 | 3/2006 | Van Antwerp et al. |
| 2007/0027385 | A1 * | 2/2007 | Brister et al. ................. 600/365 |
| 2007/0235331 | A1 * | 10/2007 | Simpson et al. ......... 204/403.01 |
| 2008/0026473 | A1 * | 1/2008 | Wang et al. ..................... 436/63 |
| 2011/0077490 | A1 * | 3/2011 | Simpson et al. .............. 600/345 |

FOREIGN PATENT DOCUMENTS

| | | |
|---|---|---|
| JP | 60173452 | 9/1985 |
| WO | 93/15651 | 8/1993 |
| WO | 9315651 | 8/1993 |
| WO | 9807458 | 2/1998 |
| WO | 9808553 | 3/1998 |
| WO | 9810805 | 3/1998 |
| WO | 9819627 | 5/1998 |
| WO | 9856293 | 12/1998 |
| WO | 9921703 | 5/1999 |
| WO | 9922993 | 5/1999 |
| WO | 9945375 | 9/1999 |
| WO | 9945387 | 9/1999 |
| WO | 9956613 | 11/1999 |
| WO | 0158348 | 8/2001 |
| WO | 02053764 | 7/2002 |
| WO | 2006127694 | 11/2006 |
| WO | 2009/121026 | 10/2009 |
| WO | 2009121026 | 10/2009 |

OTHER PUBLICATIONS

International Search Report mailed Apr. 28, 2011, International application No. PCT/US2010/060883, International filed Dec. 16, 2010.

Kimura, J. et al., 1989, "Evaluation of an Albumin-Based, Spin-Coated, Enzyme-Immobilized Membrane for an Isfet Glucose Sensor by Computer Simulation," Journal of Membrane Science, 43:291-305.

Koudelka, M., et al., "Planar Amperometric Enzyme-Based Glucose Microelectrode," Sensors and Actuators, 18 (Elsevier Sequoia, The Netherlands—1989), pp. 157-165.

Koudelka, M., et al., "In-vivo Behaviour of Hypodermically Implanted Microfabricated Glucose Sensors," Biosensors & Bioelectronics 6, (Elsevier Science Publishers Ltd., England—1991) pp. 31-36.

Mastrototaro, John J., et al., "An electroenzymatic glucose sensor fabricated on a flexible substrate," Sensors and Actuators B.5 (Elsevier Sequoia 1991), p. 139-144.

"3M Specifications and Design Guidelines, Microflex Circuits for IC Interconnect Solutions," pp. 1-32 (the entire document), 1997 (3M Electronic Products Division, Austin, TX).

"3M Offers More Solutions for the Semiconductor Industry", the entire document, 1997 (3M Electronic Products Division, Austin, TX).

"Microflex Solutions from 3M," the entire document, 1996 (3M Electronic Products Division, Austin, TX).

Urban, G., et al., "Miniaturized multi-enzyme biosensors integrated with pH sensors on flexible polymer carriers for in vivo applications," Biosensors & Bioelectronics 7 (Elsevier Science Publishers Ltd.—1992) pp. 733-739.

Wilke, D. et al., 1992, "Application of Redox Mediators in Enzyme Electrodes," Proc. Conf. Trends Electrochem. Biosens., pp. 155-161.

Yao, T., 1983, Analytica Chim. Acta, 148:27-33.

* cited by examiner

R = H, CH₃, CH₂CH₃

R' = H, OH, NH₂, CH₃, C₂H₅, C₃H₇, C₂H₄OH, C₂H₄NH₂

R = H, CH₃, CH₂CH₃

R' = H, OH, NH₂, CH₃, C₂H₅, C₃H₇, C₂H₄OH, C₂H₄NH₂

2-methacryloyloxyethyl phosphorylcholine (MPC)

Vinyl pyrrolidone

R = H, CH$_3$, CH$_2$CH$_3$
R' = CH$_3$, C$_2$H$_5$

Vinyl Acetate

R = H, CH$_3$, CH$_2$CH$_3$

R = CH$_3$, C$_2$H$_5$
dimethyl/ethyl methacrylamide

R = H, CH$_3$, CH$_2$CH$_3$
R' = H, CH$_3$, C$_2$H$_5$, C$_3$H$_7$, C$_2$H$_4$OH, C$_2$H$_4$NH$_2$, SiC$_3$H$_9$

R = H, CH₃, C₂H₅

R' = CH₃, C₂H₅, C₃H₇, C₂H₄ (C₆H₅), C₂H₄CF₃

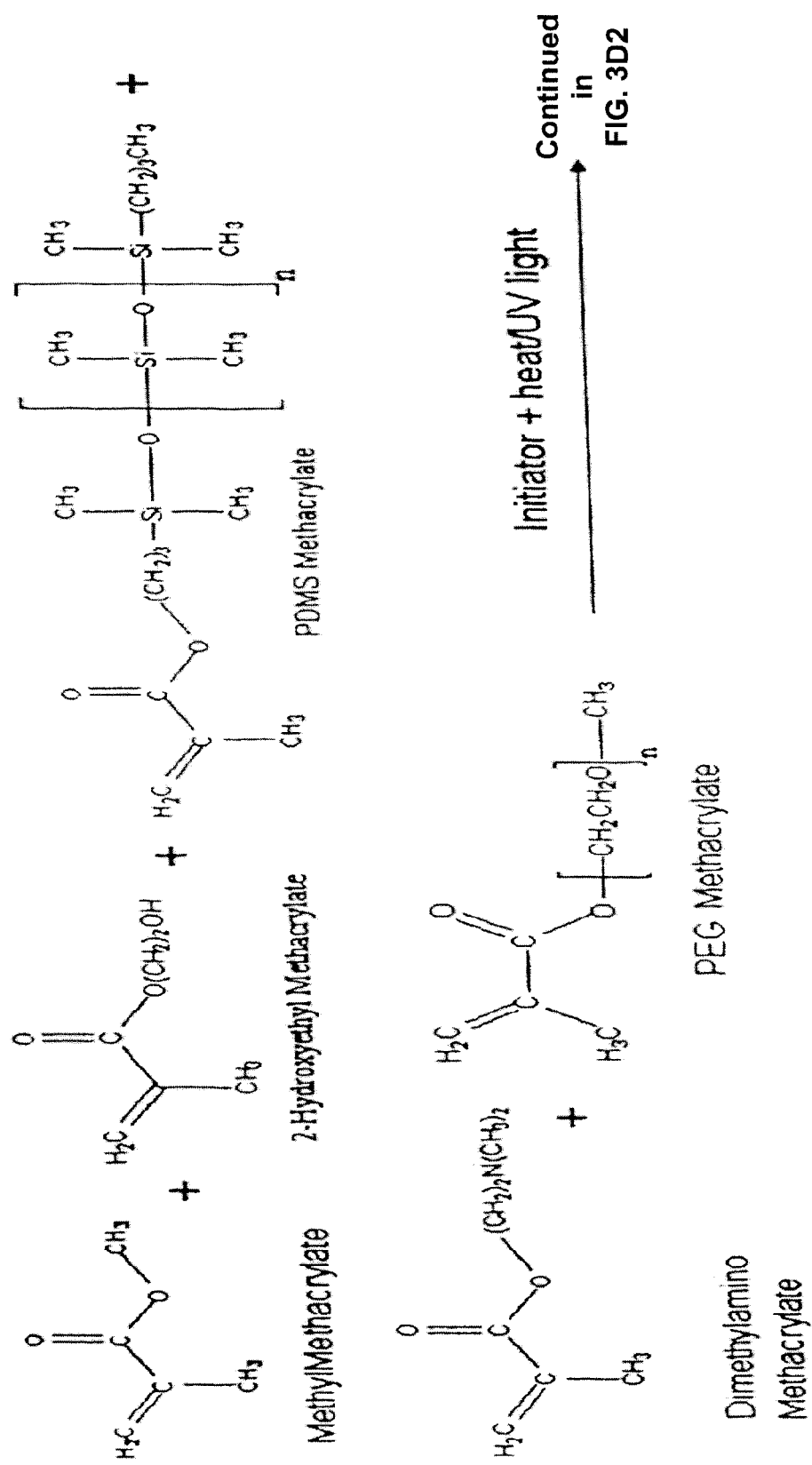
FIG. 3D1

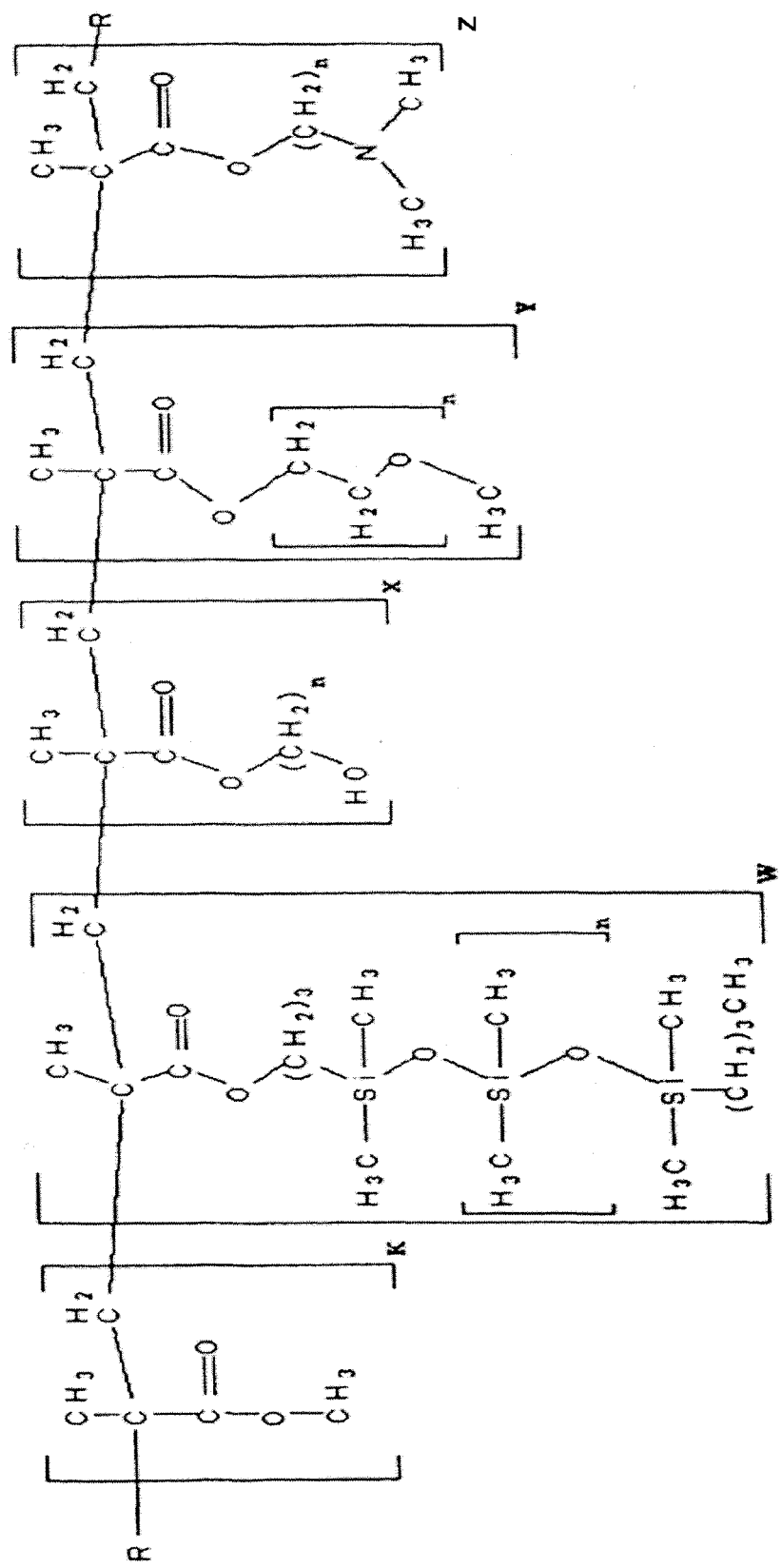
FIG. 3D2

ANALYTE SENSORS COMPRISING BLENDED MEMBRANE COMPOSITIONS AND METHODS FOR MAKING AND USING THEM

CROSS REFERENCE TO RELATED APPLICATIONS

This application is related to U.S. patent application Ser. No. 11/492,273, U.S. patent application Ser. No. 11/633,254, U.S. patent application Ser. No. 12/184,046, U.S. patent application Ser. No. 12/345,354, and U.S. patent application Ser. No. 12/572,087, the contents of each of which are herein incorporated by reference.

BACKGROUND OF THE INVENTION

1. Field of the Invention

This invention relates to biosensors such as glucose sensors used in the management of diabetes and materials for making such sensors, for example blended polymeric compositions useful for biosensor membranes.

2. Description of Related Art

Analyte sensors such as biosensors include devices that use biological elements to convert a chemical analyte in a matrix into a detectable signal. There are many types of biosensors used to detect wide variety of analytes. Perhaps the most studied type of biosensor is the amperometric glucose sensor, an apparatus commonly used to monitor glucose levels in individuals with diabetes.

A typical glucose sensor works according to the following chemical reactions:

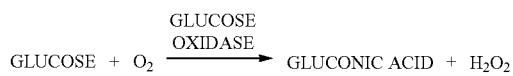

Equation 1

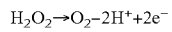

$$H_2O_2 \rightarrow O_2 - 2H^+ + 2e^-$$

Equation 2

The glucose oxidase is used to catalyze the reaction between glucose and oxygen to yield gluconic acid and hydrogen peroxide as shown in equation 1. The $H_2O_2$ reacts electrochemically as shown in equation 2, and the current is measured by a potentiostat. The stoichiometry of the reaction provides challenges to developing in vivo sensors. In particular, for optimal sensor performance, sensor signal output should be determined only by the analyte of interest (glucose), and not by any co-substrates ($O_2$) or kinetically controlled parameters such as diffusion. If oxygen and glucose are present in equimolar concentrations, then the $H_2O_2$ is stoichiometrically related to the amount of glucose that reacts at the enzyme; and the associated current that generates the sensor signal is proportional to the amount of glucose that reacts with the enzyme. If, however, there is insufficient oxygen for all of the glucose to react with the enzyme, then the current will be proportional to the oxygen concentration, not the glucose concentration. Consequently, for the sensor to provide a signal that depends solely on the concentrations of glucose, glucose must be the limiting reagent, i. e. the $O_2$ concentration must be in excess for all potential glucose concentrations. A problem with using such glucose sensors in vivo, however, is that the oxygen concentration where the sensor is implanted in vivo is low relative to glucose, a phenomena which can compromise the accuracy of sensor readings.

There are a number of approaches to solving the oxygen deficit problem. One is to make a porous membrane from a fully oxygen permeable material. However, the small amount of enzyme disposed for glucose tends to become inactivated (see, e.g. U.S. Pat. No. 4,484,987, the contents of which are incorporated by reference). Another approach is to use a homogenous polymer membrane with hydrophobic and hydrophilic regions that control oxygen and glucose permeability (see, e.g. U.S. Pat. Nos. 5,428,123; 5,322,063, 5,476, 094, the contents of which are incorporated by reference). For example, Van Antwerp et al. have developed linear polyurea membranes comprising silicone hydrophobic components that allow for a high oxygen permeability in combination with hydrophilic component that allow for a limited glucose permeability (see e.g. U.S. Pat. Nos. 5,777,060, 5,882,494 and 6,642,015).

SUMMARY OF THE INVENTION

The invention disclosed herein provides biosensors such as amperometric glucose sensors and improved materials for making such sensors. Embodiments of the invention include a sensor having a plurality of layered elements including an analyte limiting membrane comprising a blended polymeric composition. Such polymeric membranes are particularly useful in the construction of electrochemical sensors for in vivo use, and embodiments of the invention include specific biosensor configurations that incorporate these polymeric membranes. The membrane embodiments of the invention allow for a combination of desirable properties including: an enhanced hydration profile, as well as a permeability to molecules such as glucose that is stable over a range of temperatures. In addition, these polymeric membranes exhibit good mechanical properties for use as an outer polymeric membrane. Consequently, glucose sensors that incorporate such polymeric membranes show an enhanced in-vivo performance profile.

The invention disclosed herein has a number of embodiments. One embodiment of the invention is an amperometric analyte sensor apparatus comprising: a base layer; a conductive layer disposed on the base layer and comprising a working electrode; an analyte sensing layer disposed on the conductive layer (e.g. one comprising an oxidoreductase such as glucose oxidase); and an analyte modulating layer disposed on the analyte sensing layer. In this embodiment of the invention, the analyte modulating layer comprises a blended mixture of a linear polyurethane/polyurea polymer, and a branched acrylate polymer; with these polymers blended at a ratio of between 1:1 and 1:20 by weight %. Optionally in such embodiments, the linear polyurethane/polyurea polymer used to make the blended polymeric composition exhibits a permeability to glucose that decreases by between 1% and 8% per degree centigrade as temperature is increased from 22 to 40 degrees centigrade; and the branched acrylate polymer used to make the blended polymeric composition exhibits a permeability to glucose that increases by between 1% and 8% per degree centigrade as temperature is increased from 22 to 40 degrees centigrade. Typically the polymeric composition made by blending the linear polyurethane/polyurea with the branched acrylate polymer exhibits a permeability to glucose that changes less than 2% per degree centigrade over a temperature gradient of 22 to 40 degrees centigrade.

Embodiments of the invention include analyte sensor apparatus having an architecture adapted to be compatible with biological tissue as well as elements made from biocompatible materials so as to be implantable in vivo. In such embodiments of the invention, the blended polymeric composition of the analyte modulating layer facilitates in vivo hydration of the sensor so that levels of an in vivo analyte can be sensed within a short time of sensor implantation into an in vivo environment (e.g. less than 45 minutes). In addition, in certain embodiments of the invention, the blended polymeric composition of the analyte modulating layer facilitates adhesion of the layers of the sensors so as to eliminate the need for a separate adhesion promoting material disposed between various layers of the sensor (e.g. one disposed between the analyte sensing layer and the analyte modulating layer). Optionally, the sensors of the invention further include at least one of: a protein layer disposed on the analyte sensing layer; or a cover layer disposed on the analyte sensor apparatus, wherein the cover layer comprises an aperture positioned on the cover layer so as to facilitate an analyte present in an in vivo environment from contacting and diffusing through an analyte modulating layer and contacting the analyte sensing layer.

Embodiments of the invention include both materials (e.g. blended polymeric compositions) as well as architectures that designed to facilitate sensor performance. For example, in certain embodiments of the invention, the conductive layer comprises a plurality of working electrodes and/or counter electrodes and/or reference electrodes (e.g. 3 working electrodes, a reference electrode and a counter electrode), in order to, for example, avoid problems associated with poor sensor hydration and/or provide redundant sensing capabilities. Optionally, the plurality of working, counter and reference electrodes are configured together as a unit and positionally distributed on the conductive layer in a repeating pattern of units. In certain embodiments of the invention, the base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment. Typically, the sensor is operatively coupled to a sensor input capable of receiving a signal from the sensor that is based on a sensed analyte; and a processor coupled to the sensor input, wherein the processor is capable of characterizing one or more signals received from the sensor. In some embodiments of the invention, a pulsed voltage is used to obtain a signal from one or more electrodes of a sensor.

The sensors disclosed herein can be made from a wide variety of materials known in the art. In one illustrative embodiment of the invention, the analyte modulating layer comprises a polyurethane/polyurea polymer formed from a mixture comprising: a diisocyanate; a hydrophilic polymer comprising a hydrophilic diol or hydrophilic diamine; and a siloxane having an amino, hydroxyl or carboxylic acid functional group at a terminus; with this polymer then blended with a branched acrylate polymer formed from a mixture comprising: a butyl, propyl, ethyl or methyl-acrylate; an amino-acrylate; a siloxane-acrylate; and a poly(ethylene oxide)-acrylate. Optionally, additional materials can be included in these polymeric blends. For example, certain embodiments of the branched acrylate polymer are formed from a reaction mixture that includes a hydroxyl-acrylate compound.

Another embodiment of the invention is method of making an analyte sensor apparatus for implantation within a mammal comprising the steps of: providing a base layer; forming a conductive layer on the base layer, wherein the conductive layer includes a working electrode; forming an analyte sensing layer on the conductive layer, wherein the analyte sensing layer includes an oxidoreductase; forming an analyte modulating layer on the analyte sensing layer, wherein: the analyte modulating layer comprises a blended mixture of: a linear polyurethane/polyurea polymer, and a branched acrylate polymer; and the linear polyurethane/polyurea polymer and the branched acrylate polymer are blended at a ratio of between 1:1 and 1:20 by weight %; and then forming a cover layer on the analyte modulating layer. In this embodiment, the analyte modulating layer composition used to make the sensor exhibits a permeability to glucose that changes less than 2% per degree centigrade over a temperature gradient of 21 to 40 degrees centigrade. Typically, this analyte modulating layer composition comprises a first polymer formed from a mixture comprising a diisocyanate; at least one hydrophilic diol or hydrophilic diamine; and a siloxane; that is blended with a second polymer formed from a mixture comprising: a 2-(dimethylamino)ethyl methacrylate; a methyl methacrylate; a polydimethyl siloxane monomethacryloxypropyl; a poly(ethylene oxide) methyl ether methacrylate; and a 2-hydroxyethyl methacrylate. Typically in such embodiments, the analyte modulating layer composition is formed to exhibit adhesive properties that allow the analyte modulating layer composition to adhere to adjacent layers in the analyte sensing apparatus so that the analyte sensor apparatus does not include an adhesion promoting layer disposed between the analyte sensing layer and an adjacent layer.

Yet another embodiment of the invention is a composition of matter comprising a first polymer formed from a mixture comprising: a diisocyanate compound; at least one hydrophilic diol or hydrophilic diamine compound; and a siloxane compound; that is blended with a second polymer formed from a mixture comprising: 5-45 weight % of a 2-(dimethylamino)ethyl methacrylate compound; 15-55 weight % of a methyl methacrylate compound; 15-55 weight % of a polydimethyl siloxane monomethacryloxypropyl compound; 5-35 weight % of a poly(ethylene oxide) methyl ether methacrylate compound; and 1-20 weight % 2-hydroxyethyl methacrylate, with the first polymer and the second polymer blended together at a ratio between 1:1 and 1:20 weight %. Typically in such compositions, the linear polyurethane/polyurea polymer exhibits a permeability to glucose that decreases by between 1% and 8% per degree centigrade as temperature is increased from 22 to 40 degrees centigrade; and the branched acrylate polymer exhibits a permeability to glucose that increases by between 1% and 8% per degree centigrade as temperature is increased from 22 to 40 degrees centigrade. In such embodiments of the invention, the polymer blend exhibits a permeability to glucose that changes less than 2% per degree centigrade over a temperature range of 21 to 40 degrees centigrade.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIGS. 3D1 and 3D2 show the exemplary polymerization reaction of an embodiment of a branched acrylate polymer. While the embodiment shown in FIGS. 3D1 and 3D2 uses methacrylates as illustrative monomers, those of skill in the art understand that two or more monomers in this representative formula can be replaced with compounds such as ethylacrylates or acrylates (e.g. methyl methacrylate can be replaced with methyl acrylate or ethyl methacrylate).

In FIG. 4A, the signals obtained from glucose sensors under various conditions are illustrated in a graphical format. In FIG. 4B, the signals obtained from glucose sensors under various conditions are illustrated in a graphical format.

DETAILED DESCRIPTION OF THE EMBODIMENTS

Figure 1:
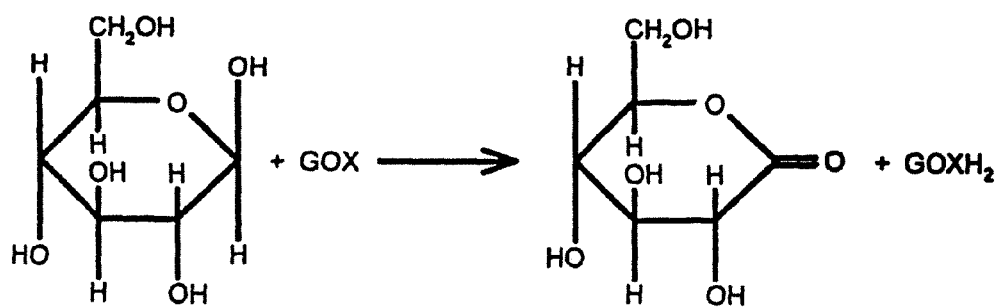
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).
Figure 1:
Figure 1:
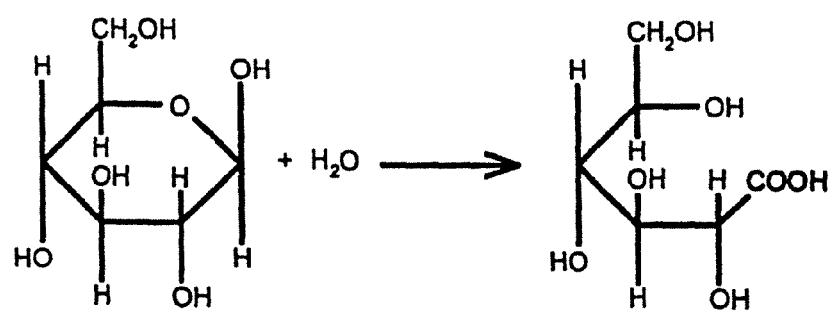

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. "50 mol %") are understood to be modified by the term "about".

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The terms "interferents" and "interfering species/compounds" are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured so as to produce spurious signals.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The terms "electrochemically reactive surface" and "electroactive surface" as used herein are broad terms and are used in their ordinary sense, including, without limitation, the surface of an electrode where an electrochemical reaction takes place. In one example, a working electrode (e.g. one comprised of platinum black) measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

As discussed in detail below, embodiments of the invention relate to the use of an electrochemical sensor that exhibits a novel constellation of elements including a blended polymeric analyte modulating membrane having a unique set of technically desirable material properties. The electrochemical sensors of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors comprise a blended polymeric membrane surrounding the enzyme through which an analyte migrates prior to reacting with the enzyme. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their biospecificity. Embodiments of the invention described herein can be adapted and implemented with a wide variety of known electrochemical sensors, including for example, U.S. Patent Application No. 20050115832, U.S. Pat. Nos. 6,001, 067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, W003/036310 WO 08/042625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. analyte modulating membranes made from blended polymeric compositions) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

Specific aspects of embodiments of the invention are discussed in detail in the following sections.

I. Typical Elements, Configurations and Analyte Sensors of the Invention

A. Optimized Sensor Elements of the Invention

A wide variety of sensors and sensor elements are known in the art including amperometric sensors used to detect and/or measure biological analytes such as glucose. Many glucose sensors are based on an oxygen (Clark-type) amperometric transducer (see, e.g. Yang et al., Electroanalysis 1997, 9, No. 16: 1252-1256; Clark et al., Ann. N.Y. Acad. Sci. 1962, 102, 29; Updike et al., Nature 1967, 214,986; and Wilkins et al., Med. Engin. Physics, 1996, 18, 273.3-51). A number of in vivo glucose sensors utilize hydrogen peroxide-based amperometric transducers because such transducers are relatively easy to fabricate and can readily be miniaturized using conventional technology. One problem associated with the use of certain amperometric transducers, however, include a suboptimal reaction stoichiometry. As discussed in detail below, these problems are addressed by using the blended polymeric membrane(s) disclosed herein, membranes which can modulate the transport properties of different compounds whose reaction creates a signal at the hydrogen peroxide-based amperometric transducing element. Consequently, these membranes can be used for example with a variety of $H_2O_2$ based analyte sensors that benefit from optimized reaction stoichiometries. As noted above, embodiments of the invention include sensor membranes made from blended polymer compositions. As is known in the art, a polymer comprises a long or larger molecule consisting of a chain or network of many repeating units, formed by chemically bonding together many identical or similar small molecules called monomers. A copolymer or heteropolymer is a polymer derived from two (or more) monomeric species, as opposed to a homopolymer where only one monomer is used. Copolymers may also be described in terms of the existence of or arrangement of branches in the polymer structure. Linear copolymers consist of a single main chain whereas branched copolymers consist of a single main chain with one or more polymeric side chains. Sensor membranes made from blended polymeric compositions disclosed herein can optimize analyte sensor function including sensor sensitivity, stability and hydration profiles. In addition, by optimizing the stoichiometry of reactant species over a range of sensor temperatures, the membranes disclosed herein can optimize the chemical reactions that produce the critical measurable signals that correlate with the levels of an analyte of interest (e.g. glucose). The following sections describe illustrative sensor elements, sensor configurations and methodological embodiments of the invention.

Figure 2A:
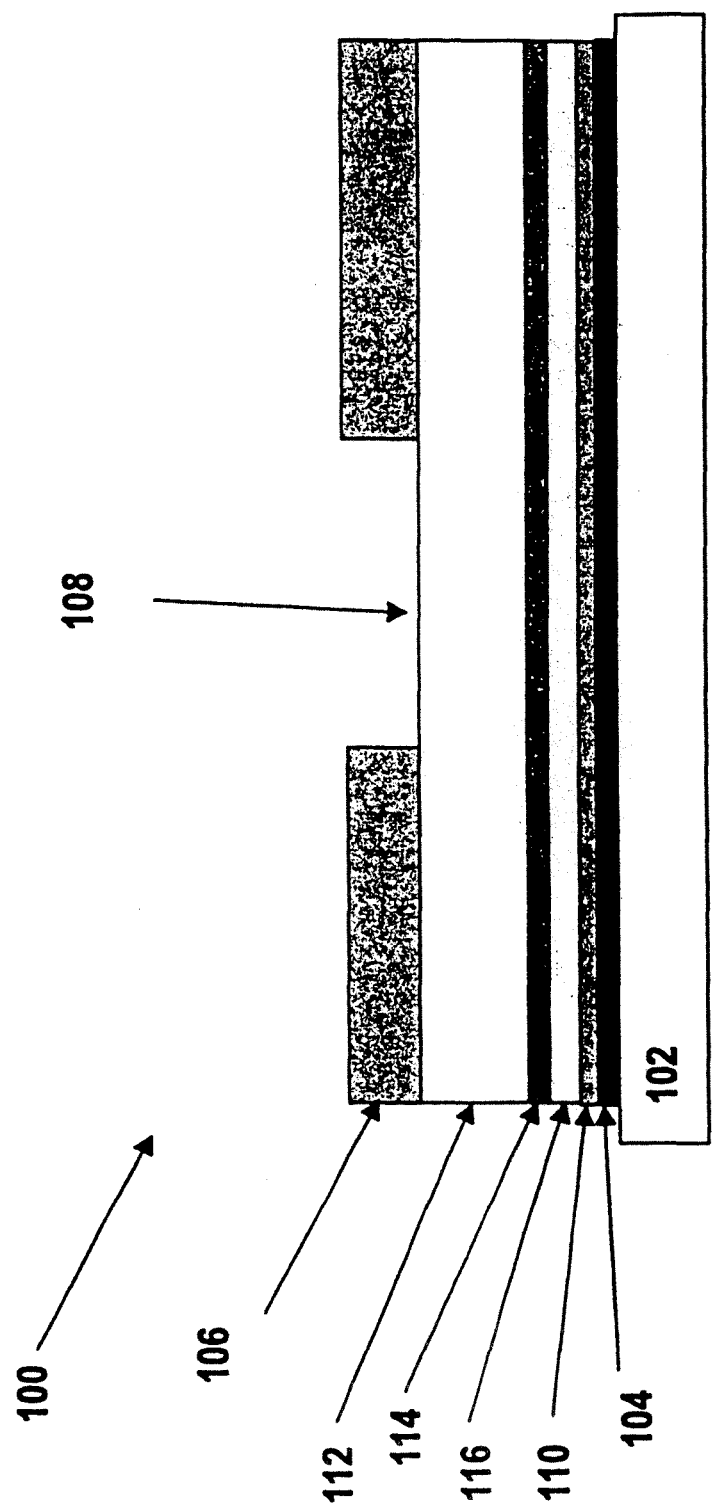
FIG. 2A provides a diagrammatic view of one embodiment of an amperometric analyte sensor to which an interference rejection membrane can be added.

Certain amperometric sensor design used with embodiments of the invention comprise a plurality of layered elements including for example a base layer having an electrode, an analyte sensing layer (e.g. one comprising glucose oxidase) and an analyte modulating layer that functions in analyte diffusion control (e.g. to modulate the amounts of glucose and oxygen exposed to the analyte sensing layer). One such sensor embodiment is shown in FIG. 2A. Layered sensor designs that incorporate the blended polymeric compositions disclosed herein as the analyte modulating layer exhibit a constellation of material properties that overcome challenges observed in a variety of sensors including electrochemical glucose sensors that are implanted in vivo. For example, sensors designed to measure analytes in aqueous environments (e.g. those implanted in vivo) typically require wetting of the layers prior to and during the measurement of accurate analyte reading. Because the properties of a material can influence the rate at which it hydrates, the material properties of membranes used in aqueous environments ideally will facilitate sensor wetting to, for example, minimize the time period between the sensor's introduction into an aqueous environment and its ability to provide accurate signals that correspond to the concentrations of an analyte in that environment. Embodiments of the invention that comprise blended polymeric compositions address such issues by facilitating sensor hydration.

Moreover, with electrochemical glucose sensors that utilize the chemical reaction between glucose and glucose oxidase to generate a measurable signal, the material of the analyte modulating layer should not exacerbate (and ideally should diminish) what is known in the art as the "oxygen deficit problem". Specifically, because glucose oxidase based sensors require both oxygen ($O_2$) as well as glucose to generate a signal, the presence of an excess of oxygen relative to glucose, is necessary for the operation of a glucose oxidase based glucose sensor. However, because the concentration of oxygen in subcutaneous tissue is much less than that of glucose, oxygen can be the limiting reactant in the reaction between glucose, oxygen, and glucose oxidase in a sensor, a situation which compromises the sensor's ability to produce a signal that is strictly dependent on the concentration of glucose. In this context, because the properties of a material can influence the rate at which compounds diffuse through that material to the site of a measurable chemical reaction, the material properties of an analyte modulating layer used in electrochemical glucose sensors that utilize the chemical reaction between glucose and glucose oxidase to generate a measurable signal, should not for example, favor the diffusion of glucose over oxygen in a manner that contributes to the oxygen deficit problem. Embodiments of the invention that comprise the blended polymeric compositions disclosed herein do not contribute to, and instead function to ameliorate, the oxygen deficit problem.

In addition, sensor designs that use the blended polymeric compositions disclosed herein as a analyte modulating layer can also overcome complications observed with the use of sensor materials that can exhibit different diffusion profiles (e.g. a rate at which an analyte diffuses therethrough) at different temperatures. In particular, for optimized sensor performance, sensor signal output over a range of temperatures should be determined only by the levels of analyte of interest (e.g. glucose), and not by any co-substrates (e.g. $O_2$) or kinetically controlled parameters (e.g. diffusion). As is known in the art however, the diffusion of compounds through a polymeric matrix can be temperature dependent. In situations where an analyte (e.g. glucose) diffuses through a polymer to react a site where it reacts with another compound (e.g. glucose oxidase), such temperature dependent diffusion profiles can influence the stoichiometry of the reaction relied upon to generate the sensor signal, thereby confounding artisans' efforts to make sensor signal output depend only on the concentration of an analyte of interest over a range of temperatures. Analyte modulating compositions made from materials having an analyte (e.g. glucose) diffusion profile that is stable over a range of temperatures (e.g. from 22 to 40 degrees centigrade) consequently address such issues.

The invention disclosed herein provides blended polymeric compositions useful for example as membranes for biosensors such as amperometric glucose sensors. Embodiments of the invention include for example a sensor having a plurality of layered elements including an analyte limiting membrane comprising a blended polymeric composition. Such polymeric membranes are particularly useful in the construction of electrochemical sensors for in vivo use. The membrane embodiments of the invention allow for a combination of desirable properties including: an enhanced hydration profile as well as a permeability to molecules such as glucose that is stable over a range of temperatures. In addition, these polymeric membranes exhibit good mechanical properties for use as an outer polymeric membrane. Consequently, glucose sensors that incorporate such polymeric membranes show a highly desirable in-vivo performance profile.

The invention disclosed herein has a number of embodiments. One embodiment of the invention is an amperometric analyte sensor apparatus comprising: a base layer; a conductive layer disposed on the base layer and comprising a working electrode; an analyte sensing layer disposed on the conductive layer (e.g. one comprising an oxidoreductase such as glucose oxidase); and an analyte modulating layer disposed on the analyte sensing layer. In this embodiment of the invention, the analyte modulating layer comprises a blended mixture of a linear polyurethane/polyurea polymer, and a branched acrylate polymer; with these polymers blended at a ratio of at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20 by weight %. Typically in such embodiments, the linear polyurethane/polyurea polymer used to make homogeneous blended polymeric compositions that exhibit a permeability to glucose that decreases by between 1% and 8% per degree centigrade as temperature is increased from 22 to 40 degrees centigrade; and the branched acrylate polymer used to make the blended polymeric composition exhibits a permeability to glucose that increases by between 1% and 8% per degree centigrade as temperature is increased from 22 to 40 degrees centigrade. Typically the polymeric composition that results from blending the linear polyurethane/polyurea with the branched acrylate polymer exhibits a permeability to glucose that changes less than 2% per degree centigrade over a temperature range of 22 to 40 degrees centigrade.

Embodiments of the invention blend polymers having opposite yet complementary glucose diffusion profiles to generate an analyte modulating composition having a stabilized glucose diffusion profile. Specifically, certain polyurea and/or polyurethane analyte modulating compositions (e.g. those disclosed in U.S. Pat. Nos. 5,777,060, 5,882,494 and 6,642,015) have a glucose diffusion profile that decreases as the temperature increases. These linear polyurea and polyurethane polymers can exhibit about a −3% per degree C. in glucose signal change from 22 to 40 degrees centigrade (i.e. the signal observed from a given concentration of glucose decreases about 3% per degree C. as temperature is increased from 22 to 40 degrees centigrade). In contrast, the branched acrylate polymers disclosed herein have a glucose diffusion profile that decreases as the temperature increases. These branched acrylate polymers exhibit about a +3% per degree C. in glucose signal change from 22 to 40 degrees centigrade (i.e. the signal observed from a given concentration of glucose increases about 3% per degree C. as temperature is increased from 22 to 40 degrees centigrade). When the linear polyurethane/polyurea polymer and the branched acrylate polymer are blended together however, the opposite temperature effects are cancelled out with the result that the blended membrane becomes an essentially non-temperature dependent glucose limiting polymer from 22 to 40 degrees centigrade.

By modulating the relative amounts of the linear polyurea/polyurethane and the branched acrylate polymers in a blend, one can ameliorate temperature dependent glucose permeability profiles that are observed with certain polymer matrices. Due to the interactions between two different polymers, the blend ratio is not necessarily the theoretical ratio of 1:1 and has been determined empirically to be between 1:1 and 1:20 by weight %. In this context, either polymer can be in excess and "1:20" therefore encompasses blends where the branched acrylate is present in a ¹⁄₂₀th fraction (0.05) as well as blends where the linear polyurea/polyurethane is present in a ¹⁄₂₀th fraction. In situations where it is desirable a glucose sensor generate a relatively low signal in response to glucose, the linear polyurea/polyurethane and the branched acrylate can be blended together at a ratio where the linear polyurea/polyurethane is in excess, such as a 2:1 ratio. In situations where it is desirable that the sensor generate a relatively high signal in response to glucose, the linear polyurea/polyurethane and the branched acrylate can be blended together at a ratio where the branched acrylate is in excess, such as a 1:2 ratio. Altering these polymer ratios can also have benefits in other contexts. For example, an increased relative amount of branched acrylate polymer in the polymer blend can enhance the adhesion between blended polymer membrane and a proximal material or layer in a sensor (e.g. a GOx layer).

Embodiments of the invention include analyte sensor apparatus having an architecture adapted to be compatible with biological tissue as well as elements made from biocompatible materials so as to be implantable in vivo. In such embodiments of the invention, a homogeneously blended polymeric composition of the analyte modulating layer facilitates in vivo hydration of the sensor so that levels of an in vivo analyte can be sensed less than 45 minutes or less than 30 minutes (including a 20 min initialization process) after sensor implantation into an in vivo environment. In addition, in certain embodiments of the invention, the blended polymeric composition of the analyte modulating layer facilitates adhesion of the layers of the sensors so as to eliminate the need for a separate layer of an adhesion promoting material between various layers of the sensor (e.g. one disposed between the analyte sensing layer and the analyte modulating layer). Optionally, the sensors of the invention further include at least one of: a protein layer disposed on the analyte sensing layer; or a cover layer disposed on the analyte sensor apparatus, wherein the cover layer comprises an aperture positioned on the cover layer so as to facilitate an analyte present in an in vivo environment from contacting and diffusing through an analyte modulating layer; and contacting the analyte sensing layer.

Embodiments of the invention include both materials (e.g. blended polymeric compositions) as well as architectures that designed to facilitate sensor performance. For example, in certain embodiments of the invention, the conductive layer comprises a plurality of working electrodes and/or counter electrodes and/or reference electrodes (e.g. 3 working electrodes, a reference electrode and a counter electrode), in order to, for example, avoid problems associated with poor sensor hydration and/or provide redundant sensing capabilities. Optionally, the plurality of working, counter and reference electrodes are configured together as a unit and positionally distributed on the conductive layer in a repeating pattern of units. In certain embodiments of the invention, the base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment. Typically, the sensor is operatively coupled to a sensor input capable of receiving a signal from the sensor that is based on a sensed analyte; and a processor coupled to the sensor input, wherein the processor is capable of characterizing one or more signals received from the sensor. In some embodiments of the invention, a pulsed voltage is used to obtain a signal from one or more electrodes of a sensor.

The sensors disclosed herein can be made from a wide variety of materials known in the art. In one illustrative embodiment of the invention, the analyte modulating layer comprises a polyurethane/polyurea polymer formed from a mixture comprising: a diisocyanate; a hydrophilic polymer comprising a hydrophilic diol or hydrophilic diamine; and a siloxane having an amino, hydroxyl or carboxylic acid functional group at a terminus; with this polymer then blended with a branched acrylate polymer formed from a mixture comprising: a butyl, propyl, ethyl or methyl-acrylate; an amino-acrylate; a siloxane-acrylate; and a poly(ethylene oxide)-acrylate. Optionally, additional materials can be included in these polymeric blends. For example, certain embodiments of the branched acrylate polymer are formed from a reaction mixture that includes a hydroxyl-acrylate compound (e.g. 2-hydroxyethyl methacrylate).

In a specific embodiment of the invention, the analyte modulating layer comprises a polyurethane/polyurea polymer formed from a mixture comprising a diisocyanate; a hydrophilic polymer comprising a hydrophilic diol or hydrophilic diamine; and a siloxane having an amino, hydroxyl or carboxylic acid functional group at a terminus, with this polyurethane/polyurea polymer being blended with a branched acrylate polymer formed from a mixture comprising a methyl methacrylate; a 2-(dimethylamino)ethyl methacrylate; a polydimethyl siloxane monomethacryloxypropyl; a poly(ethylene oxide) methyl ether methacrylate; and a 2-hydroxyethyl methacrylate. Typically, the first polymer is formed from a mixture comprising: a diisocyanate compound (typically about 50 mol % of the reactants in the mixture); at least one hydrophilic diol or hydrophilic diamine compound (typically about 17 to 45 mol % of the reactants in the mixture); and a siloxane compound. Optionally the first polyurethane/polyurea polymer comprises 45-55 mol % (e.g. 50 mol %) of a diisocyanate (e.g. 4,4'-diisocyanate), 10-20 (e.g. 12.5 mol %) mol % of a siloxane (e.g. polymethylhydrosiloxane, trimethylsilyl terminated), and 30-45 mol % (e.g. 37.5 mol %) of a hydrophilic diol or hydrophilic diamine compound (e.g. polypropylene glycol diamine having an average molecular weight of 600 Daltons, Jeffamine 600). This first polyurethane/polyurea polymer is blended with a second polymer formed from a mixture comprising: 5-45 weight % of a 2-(dimethylamino)ethyl methacrylate compound; 15-55 weight % of a methyl methacrylate compound; 15-55 weight % of a polydimethyl siloxane monomethacryloxypropyl compound; 5-35 weight % of a poly(ethylene oxide) methyl ether methacrylate compound; and 1-20 weight % 2-hydroxyethyl methacrylate, with the first polymer and the second polymer blended together at a ratio between 1:1 and 1:20 weight %.

Another embodiment of the invention is method of making an analyte sensor apparatus for implantation within a mammal comprising the steps of: providing a base layer; forming a conductive layer on the base layer, wherein the conductive layer includes a working electrode; forming an analyte sensing layer on the conductive layer, wherein the analyte sensing layer includes an oxidoreductase; forming an analyte modulating layer on the analyte sensing layer, wherein: the analyte modulating layer comprises a blended mixture of: a linear polyurethane/polyurea polymer, and a branched acrylate polymer; and the linear polyurethane/polyurea polymer and the branched acrylate polymer are blended at a ratio of between 1:1 and 1:20 by weight %; and then forming a cover layer on the analyte modulating layer. In this embodiment, the analyte modulating layer composition used to make the sensor exhibits a permeability to glucose that changes less than 2% per degree centigrade over a temperature range of 21 to 40 degrees centigrade. Typically, this analyte modulating layer composition comprises a first polymer formed from a mixture comprising a diisocyanate; at least one hydrophilic diol or hydrophilic diamine; and a siloxane; that is blended with a second polymer formed from a mixture comprising: a 2-(dimethylamino)ethyl methacrylate; a methyl methacrylate; a polydimethyl siloxane monomethacryloxypropyl; a poly(ethylene oxide)methyl ether methacrylate; and a 2-hydroxyethyl methacrylate. Typically in such embodiments, the analyte modulating layer composition is formed to exhibit adhesive properties that allow the analyte modulating layer composition to adhere to adjacent layers in the analyte sensing apparatus so that the analyte sensor apparatus does not include an adhesion promoting layer disposed between the analyte sensing layer and an adjacent layer.

Yet another embodiment of the invention is a composition of matter comprising a first polymer formed from a mixture comprising: a diisocyanate compound; at least one hydrophilic diol or hydrophilic diamine compound; and a siloxane compound; that is blended with a second polymer formed from a mixture comprising: 5-45 weight % of a 2-(dimethylamino)ethyl methacrylate compound; 15-55 weight % of a methyl methacrylate compound; 15-55 weight % of a polydimethyl siloxane monomethacryloxypropyl compound; 5-35 weight % of a poly(ethylene oxide) methyl ether methacrylate compound; and 1-20 weight % 2-hydroxyethyl methacrylate, with the first polymer and the second polymer blended together at a ratio between 1:1 and 1:20 weight %. Optionally, the blended membrane casting solution used to make the membrane is a blend of isopropyl alcohol and tetrahydrofuran. Typically in such compositions, the linear polyurethane/polyurea polymer exhibits a permeability to glucose that decreases by between 1% and 8% per degree centigrade as temperature is increased from 22 to 40 degrees centigrade; and the branched acrylate polymer exhibits a permeability to glucose that increases by between 1% and 8% per degree centigrade as temperature is increased from 22 to 40 degrees centigrade. In such embodiments of the invention, the polymer blend exhibits a permeability to glucose that changes less than 2% per degree centigrade over a temperature range of 21 to 40 degrees centigrade.

A related embodiment of the invention is an acrylate-based composition suitable for use with an analyte sensor, the composition comprising both a branched-chain copolymer and a linear-chain copolymer blended together at a specific ratio between 1:1 and 1:20 weight %. Typically in this embodiment, one copolymer has a positive temperature slope to the permeability (higher temperature, higher permeability), while the other copolymer has a negative temperature slope to the permeability (higher temperature, lower permeability). The temperature-dependent permeability coefficient of blended copolymer membrane is then controlled by the mixing ratio of those two copolymers. Typically, the temperature-dependent permeability coefficient of blended copolymer membrane is controlled so as to be +/−2%, 1%, 0.5% or 0.2% per degree C. from 22° C. to 40° C. In embodiments of the invention, one copolymer can have a high (glucose) permeability coefficient and the other copolymer can have a low glucose permeability coefficient, with the typical permeability ratio of the two copolymers being more than 10. In certain embodiments of the invention, the blended membrane composition comprises at least one compound having an affinity domain, wherein the affinity domain comprises a secondary or tertiary amine polymer side chains having an affinity for an interfering species (e.g. acetaminophen and/or ascorbic acid). In some embodiments, one or more polymers that comprise the blended membrane composition includes constituents such as: a 2-(dimethylamino) ethyl methacrylate or its derivatives; a vinyl-pyrrolidone or its derivatives; a tert-butylamino ethyl methacrylate or its derivatives. Optionally, one or more polymers that comprise the blended membrane composition comprises at least 1% (and up to up to 48%) by weight secondary or tertiary amines.

As noted above, the invention disclosed herein comprises a composition made by blending a linear polyurethane/polyurea polymer and the branched acrylate polymer which can for example as a analyte modulating membrane in a biosensor. From the above description, it will be apparent to one of skill in the art that the discovery underlying the present invention is the use of blended polymeric compositions, in the formation of biocompatible membranes. Membrane embodiments produced from these components are homogeneous and are useful for coating a number of biosensors and devices designed for subcutaneous implantation. Descriptions of embodiments of the linear polyurea/polyurethane polymers as well as the branched acrylate polymers are provided in the following paragraphs as well as the Examples below.

Linear Polyurethane/Polyurea Polymers

One polymeric composition used in embodiments of the present invention is a polyurethane/polyurea polymer. As used herein, the term "polyurethane/polyurea polymer" refers to a polymer containing urethane linkages, urea linkages or combinations thereof. As is known in the art, polyurethane is a polymer consisting of a chain of organic units joined by urethane (carbamate) links. Polyurethane polymers are typically formed through step-growth polymerization by reacting a monomer containing at least two isocyanate functional groups with another monomer containing at least two hydroxyl (alcohol) groups in the presence of a catalyst. Polyurea polymers are derived from the reaction product of an isocyanate component and a diamine. Typically, such polymers are formed by combining diisocyanates with alcohols and/or amines. For example, combining isophorone diisocyanate with PEG 600 and aminopropyl polysiloxane under polymerizing conditions provides a polyurethane/polyurea composition having both urethane (carbamate) linkages and urea linkages. Such polymers are well known in the art and described for example in U.S. Pat. Nos. 5,777,060, 5,882,494 and 6,632,015, and PCT publications WO 96/30431; WO 96/18115; WO 98/13685; and WO 98/17995, the contents of each of which is incorporated by reference.

The polyurethane/polyurea compositions of the invention are prepared from biologically acceptable polymers whose hydrophobic/hydrophilic balance can be varied over a wide range to control the ratio of the diffusion coefficient of oxygen to that of glucose, and to match this ratio to the design requirements of electrochemical glucose sensors intended for in vivo use. Such compositions can be prepared by conventional methods by the polymerization of monomers and polymers noted above. The resulting polymers are soluble in solvents such as acetone or ethanol and may be formed as a membrane from solution by dip, spray or spin coating.

Diisocyanates useful in this embodiment of the invention are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6hexamethylene diisocyanate (HDI), trimethylhexamethylene diisocyanate (TMDI), trans1,4-cyclohexane diisocyanate (CHDI), 1,4-cyclohexane bis(methylene isocyanate) (BDI), 1,3-cyclohexane bis(methylene isocyanate) (H6 XDI), isophorone diisocyanate (IPDI) and 4,4'-methylenebis(cyclohexyl isocyanate) ($H_2$ MDI). In some embodiments, the diisocyanate is isophorone diisocyanate, 1,6-hexamethylene diisocyanate, or 4,4'methylenebis(cyclohexyl isocyanate). A number of these diisocyanates are available from commercial sources such as Aldrich Chemical Company (Milwaukee, Wis., USA) or can be readily prepared by standard synthetic methods using literature procedures.

The quantity of diisocyanate used in the reaction mixture for the polyurethane/polyurea polymer compositions is typically about 50 mol % relative to the combination of the remaining reactants. More particularly, the quantity of diisocyanate employed in the preparation of the polyurethane/polyurea polymer will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), b moles of a silicone polymer having functionalized termini, and c moles of a chain extender, such that x=a+b+c, with the understanding that c can be zero.

Figure 4A:
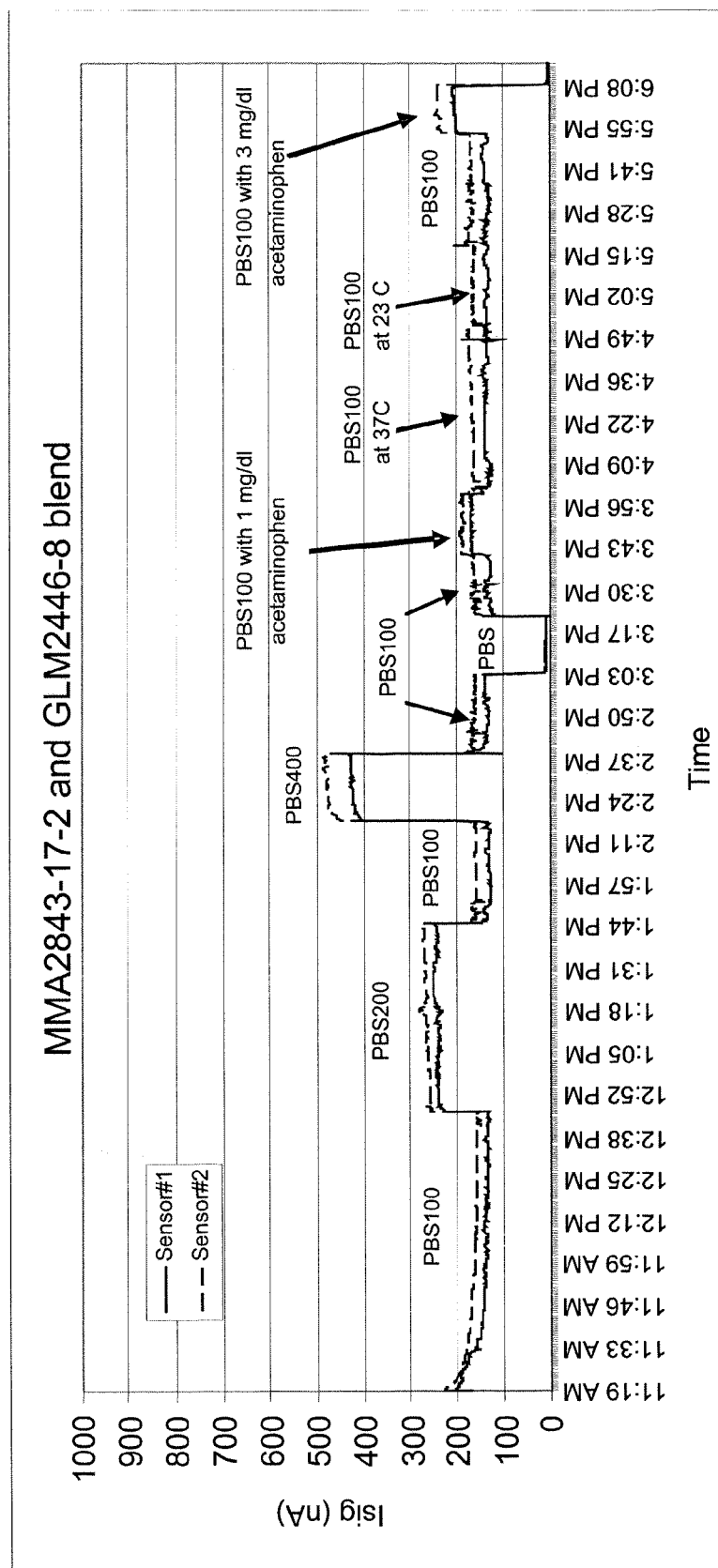
FIG. 4A shows data obtained from glucose sensors comprising an analyte modulating membrane made from a branched acrylate copolymer (designation MMA2843-17-2) blended with a linear polyurethane/polyurea copolymer (designation GLM2446-8) at 1 to 2 ratio in a tetrahydrofuran (THF) solvent.
Figure 4B:
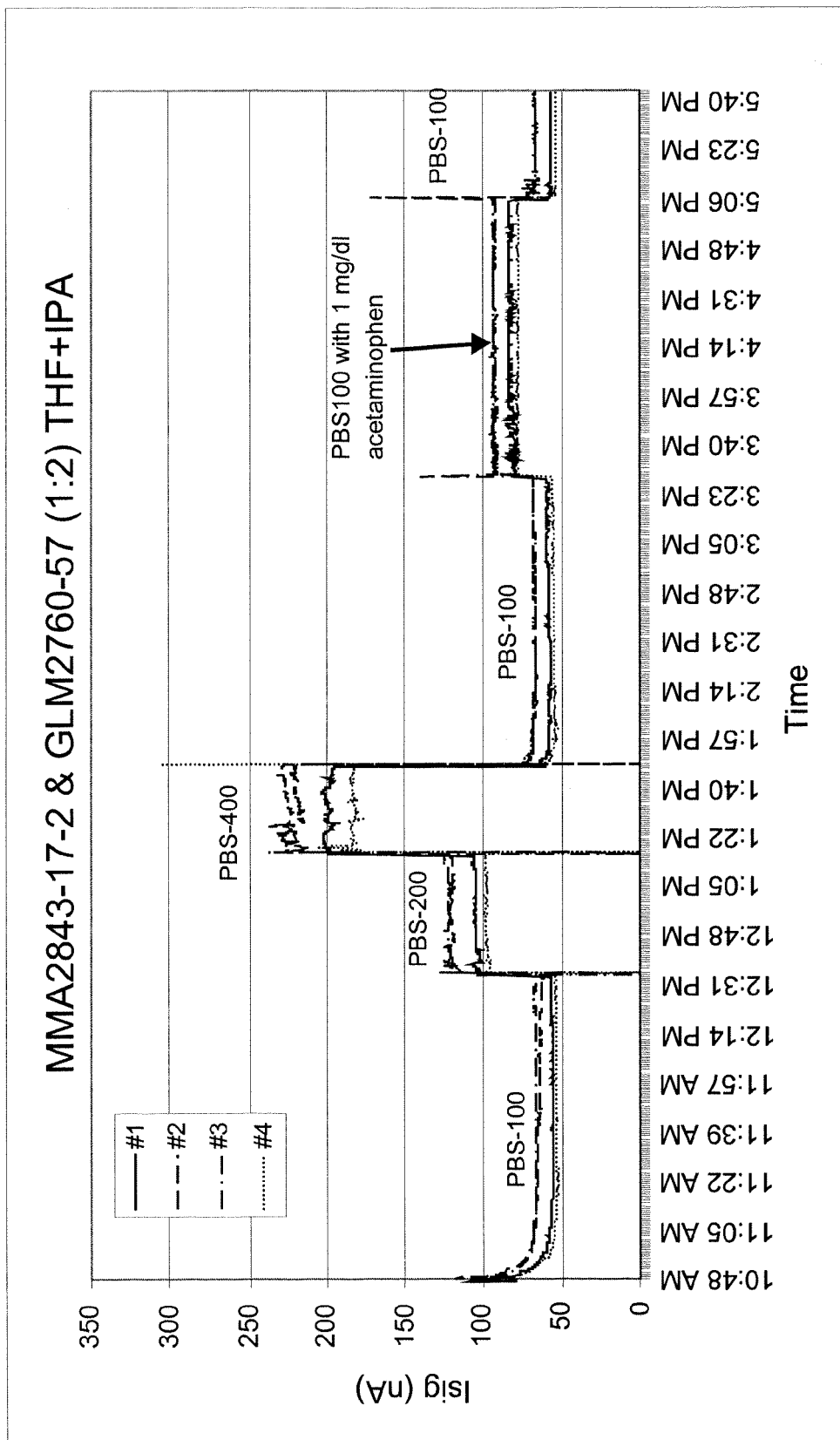
FIG. 4B shows data obtained from glucose sensors comprising an analyte modulating membrane made from a branched acrylate copolymer (designation MMa2843-17-2) blended with linear polyurethane/polyurea copolymer (designation GLM2760-57) at 1 to 2 ratio in a THF/isopropyl alcohol (IPA) mixed solvent.

Another reactant used in the preparation of the polyurethane/polyurea polymers described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol. As used herein, the term "poly(alkylene)glycol" refers to polymers of lower alkylene glycols such as poly(ethylene)glycol, poly(propylene)glycol and polytetramethylene ether glycol (PTMEG). The term "polyester-based polyol" refers to a polymer in which the R group is a lower alkylene group such as ethylene, 1,3-propylene, 1,2-propylene, 1,4-butylene, 2,2-dimethyl-1,3-propylene, and the like (e.g. as depicted in FIG. 4 of U.S. Pat. No. 5,777,060). One of skill in the art will also understand that the diester portion of the polymer can also vary from the six-carbon diacid shown. For example, while FIG. 4 of U.S. Pat. No. 5,777,060 illustrates an adipic acid component, the present invention also contemplates the use of succinic acid esters, glutaric acid esters and the like. The term "polycarbonate polyol" refers those polymers having hydroxyl functionality at the chain termini and ether and carbonate functionality within the polymer chain. The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a some hydrophilic diamine is a "diamino poly(oxyalkylene)" which is poly(alkylene)glycol in which the terminal hydroxyl groups are replaced with amino groups. The term "diamino poly(oxyalkylene)" also refers to poly(alkylene)glycols which have aminoalkyl ether groups at the chain termini. One example of a suitable diamino poly(oxyalkylene) is poly(propylene glycol)bis(2-aminopropyl ether). A number of the above polymers can be obtained from Aldrich Chemical Company. Alternatively, conventional methods known in the art can be employed for their synthesis.

The amount of hydrophilic polymer which is used to make the linear polymer compositions will typically be about 10% to about 80% by mole relative to the diisocyanate which is used. Typically, the amount is from about 20% to about 60% by mole relative to the diisocyanate. When lower amounts of hydrophilic polymer are used, it is common to include a chain extender.

Silicone containing polyurethane/polyurea polymers which are useful in the present invention are typically linear, have excellent oxygen permeability and essentially no glucose permeability. Typically, the silicone polymer is a polydimethylsiloxane having two reactive functional groups (i.e., a functionality of 2). The functional groups can be, for example, hydroxyl groups, amino groups or carboxylic acid groups, but are typically hydroxyl or amino groups. In some embodiments, combinations of silicone polymers can be used in which a first portion comprises hydroxyl groups and a second portion comprises amino groups. Typically, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Still others can be prepared by general synthetic methods known in the art (see, e.g. U.S. Pat. No. 5,777,060), beginning with commercially available siloxanes (United Chemical Technologies, Bristol. Pa., USA). For use in the present invention, the silicone polymers will typically be those having a molecular weight of from about 400 to about 10,000, more typically those having a molecular weight of from about 2000 to about 4000. The amount of silicone polymer which is incorporated into the reaction mixture will depend on the desired characteristics of the resulting polymer from which the biocompatible membrane are formed. For those compositions in which a lower glucose penetration is desired, a larger amount of silicone polymer can be employed. Alternatively, for compositions in which a higher glucose penetration is desired, smaller amounts of silicone polymer can be employed. Typically, for a glucose sensor, the amount of siloxane polymer will be from 10% to 90% by mole relative to the diisocyanate. Typically, the amount is from about 20% to 60% by mole relative to the diisocyanate.

In one group of embodiments, the reaction mixture for the preparation of biocompatible membranes will also contain a chain extender which is an aliphatic or aromatic diol, an aliphatic or aromatic diamine, alkanolamine, or combinations thereof (e.g. as depicted in FIG. 8 of U.S. Pat. No. 5,777,060)). Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy)benzene, meta-di(2-hydroxyethoxy)benzene, Ethacure 100® (a mixture of two isomers of 2,4-diamino-3,5-diethyltoluene), Ethacure 300® (2,4-diamino-3,5-di(methylthio)toluene), 3,3'-dichloro-4,4'diaminodiphenylmethane, Polacure® 740M (trimethylene glycol bis(para-aminobenzoate)ester), and methylenedianiline. Incorporation of one or more of the above chain extenders typically provides the resulting biocompatible membrane with additional physical strength, but does not substantially increase the glucose permeability of the polymer. Typically, a chain extender is used when lower (i.e., 10-40 mol %) amounts of hydrophilic polymers are used. In particularly some compositions, the chain extender is diethylene glycol which is present in from about 40% to 60% by mole relative to the diisocyanate.

Polymerization of the above reactants can be carried out in bulk or in a solvent system. Use of a catalyst is some, though not required. Suitable catalysts include dibutyltin bis(2-ethylhexanoate), dibutyltin diacetate, triethylamine and combinations thereof. Typically dibutyltin bis (2-ethylhexanoate is used as the catalyst. Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90-120° C. After the initial exotherm, the reaction flask can be heated at from 75° C. to 125° C., with 90° C. to 100° C. being a exemplary temperature range. Heating is usually carried out for one to two hours. Solution polymerization can be carried out in a similar manner. Solvents which are suitable for solution polymerization include dimethylformamide, dimethyl sulfoxide, dimethylacetamide, halogenated solvents such as 1,2,3-trichloropropane, and ketones such as 4-methyl-2-pentanone. Typically, THF is used as the solvent. When polymerization is carried out in a solvent, heating of the reaction mixture is typically carried out for three to four hours.

Polymers prepared by bulk polymerization are typically dissolved in dimethylformamide and precipitated from water. Polymers prepared in solvents that are not miscible with water can be isolated by vacuum stripping of the solvent. These polymers are then dissolved in dimethylformamide and precipitated from water. After thoroughly washing with water, the polymers can be dried in vacuo at about 50° C. to constant weight.

Preparation of the membranes can be completed by dissolving the dried polymer in a suitable solvent and cast a film onto a glass plate. The selection of a suitable solvent for casting will typically depend on the particular polymer as well as the volatility of the solvent. Typically, the solvent is THF, $CHCl_3$, $CH_2Cl_2$, DMF, IPA or combinations thereof. More typically, the solvent is THF or $DMF/CH_2Cl_2$ (2/98 volume %). The solvent is removed from the films, the resulting membranes are hydrated fully, their thicknesses measured and water pickup is determined. Membranes which are useful in the present invention will typically have a water pickup of about 20 to about 100%, typically 30 to about 90%, and more typically 40 to about 80%, by weight.

Oxygen and glucose diffusion coefficients can also be determined for the individual polymer compositions as well as the blended polymeric membranes of the present invention. Methods for determining diffusion coefficients are known to those of skill in the art, and examples are provided below. Certain embodiments of the biocompatible membranes described herein will typically have a oxygen diffusion coefficient ($D_{oxygen}$) of about $0.1 \times 10^{-6}$ $cm^2/sec$ to about $2.0 \times 10^{-6}$ $cm^2/sec$ and a glucose diffusion coefficient ($D_{glucose}$) of about $1 \times 10^{-9}$ $cm^2/sec$ to about $500 \times 10^{-19}$ $cm^2/sec$. More typically, the glucose diffusion coefficient is about $10 \times 10^{-9}$ $cm^2/sec$ to about $200 \times 10^{-9}$ $cm^2/sec$.

Branched Acrylate Polymers

Another polymeric composition used in embodiments of the present invention is a branched acrylate polymer, typically a silicone-based comb-copolymer. In these compositions, the silicone component typically has very low glass transition temperature (e.g. below room temperature and typically below 0° C.) and very high oxygen permeability (e.g. $1 \times 10^{-7}$ cm$^2$/sec), characteristics selected to provide advantages such as good mechanical property, higher signal-to-noise ratio, high stability, and highly accurate analysis in in-vivo environments.

Typical embodiments of the invention include a composition of matter comprising a blend of different polymers including a branched acrylate polymers comprising a hydrophilic comb-copolymer having a central chain and a plurality of side chains coupled to the central chain, wherein at least one side chain comprises a silicone moiety. As is known in the art, a comb-copolymer is one having a structure analogous to a hair comb which has a central backbone to which a plurality of teeth are attached. Such comb-copolymers have a central or main chain (that is roughly analogous to the backbone of the comb) and a plurality of side chains (that are roughly analogous to the teeth of a comb) that branch off of this central chain. This comb-copolymeric structure is shown for example in FIG. 3, where the horizontal (—C—CH$_2$—C—CH$_2$—C—CH$_2$—)$_p$ portion of the molecule is the central or main chain and the vertical for example (—C—O—C—) portions of the molecule comprise the side chains. These side chains can further have main chain to which various atoms and moieties are attached, for example the vertical (—C—O—C—C—C—Si—O—) side chain shown on the right side of the molecule shown of FIG. 3. For example the horizontal central chain of the side chain shown in this figure has hydrogen and/or methyl atoms and moieties attached thereto. In certain embodiments of the invention, the backbone of at least 1, 2, 3, 4, or 5 different side chains comprises at least 2, 3, 4, 5, 6, 7, 8, 9, 10, 11, 12, 13, 14 or 15 atoms.

The branched acrylate polymers that can be used to make the blended polymeric membranes have a number of embodiments. Typically in such embodiments, at least one side chain moiety comprising a silicone moiety comprises a Silicon atom covalently bound to an Oxygen atom (—Si—O—). In some embodiments of the invention, at least one side chain that branches off of the central chain is hydrophilic. In some embodiments of the invention, at least one side chain that branches off of the central chain is hydrophobic. In some embodiments of the invention, at least one side chain that branches off of the central chain is hydrophilic and at least one side chain that branches off of the central chain is hydrophobic. Optionally, the central chain is hydrophilic. Alternatively, the central chain can be hydrophobic, with hydrophilic properties being provided by the side chains.

In certain embodiments of the invention, the central chain comprises a polyvinyl polymer, i.e. a composition formed by polymerizing various vinyl (e.g. CH2=CH—) monomers. Examples include polyvinyl chlorides, polyvinyl acetates, and polyvinyl alcohols. Typically, such polyvinyl polymers comprise polyvinyl acetate, acrylate, acrylamide, acrylonitrile or pyrrolidone subunits. Alternatively the central chain can comprise polyethylene or polypropylene subunits. As is known in the art, such comb copolymers can be made from a variety of different methods, for example a process comprising free radical copolymerization. Typically, the comb-copolymer is made from free radical polymerization of at least one silicone material, and at least one hydrophilic material. Optionally, one or more hydrophobic materials are also used for specific applications and contexts. Illustrative methods and materials for use in making the polymeric compositions of the invention are described for example in U.S. Pat. Nos. 6,887,962, 6,809,141, 6,093,781, 5,807,937 5,708,115, 5,091,480, 5,079,298, 5,061,772, 5,503,461, 6,538,091 and 6,527,850 7,029,688, 7,029,688, 7,001,949; and U.S. Patent Application Nos. 20050143546, 20040024144 and 20030181619, 20040024144 the contents of each are herein incorporated by reference. Polymers can be coated onto biosensors using a variety of methods known in the art, for example those described in U.S. Pat. Nos. 5,882,494, 6,965,791, 6,934,572, 6,814,845, 6,741,877, 6,594,514, 6,477,395, 6,927,246, 5,422,246, 5,286,364, 6,927,033, 5,804,048, 7,003,340, 6,965,791; and U.S. Patent Application Nos. 20060128032, 20060068424, 20050208309, 20040084307, 20030171506, 20030069383, and 20010008931, the contents of each are herein incorporated by reference.

Embodiments of the invention include sensors having a membrane comprising the polymeric compositions described herein. An illustrative embodiment is an analyte sensor apparatus for implantation within a mammal, the analyte sensor apparatus comprising a base layer, a conductive layer disposed upon the base layer wherein the conductive layer includes a working electrode, an analyte sensing layer disposed on the conductive layer, wherein the analyte sensing layer detectably alters the electrical current at the working electrode in the conductive layer in the presence of an analyte, an analyte modulating layer disposed on the analyte sensing layer, wherein the analyte modulating layer modulates the diffusion of the analyte therethrough; the analyte modulating layer comprising a linear polyurethane/polyurea polymer blended with a branched acrylate comb-copolymer having a central chain and a plurality of side chains coupled to the central chain, wherein at least one side chain comprises a silicone moiety. Typically, the at least one side chain moiety comprises a Silicon atom covalently bound to an Oxygen atom (—Si—O—). Optionally, at least one side chain is hydrophilic, at least one side chain is hydrophobic or at least one chain is hydrophilic, and in addition, at least one chain is hydrophobic. Optionally, the central chain is hydrophilic. Alternatively, the central chain can be hydrophobic, with hydrophilic properties being provided by the side chains. In such analyte sensor apparatus, the membrane having this structure confers a number of desirable properties. Typically for example, the analyte modulating layer has a glucose diffusion coefficient ($D_{glucose}$) of from $1 \times 10^{-9}$ cm$^2$/sec to $1 \times 10^{-7}$ cm$^2$/sec. In addition, typically, the analyte modulating layer has a oxygen diffusion coefficient ($D_{oxygen}$) to glucose diffusion coefficient ($D_{glucose}$) ratio ($D_{oxygen}/D_{glucose}$) of 5 to 2000.

As illustrated in the Examples below, the hydrophilic comb-copolymer used in the blended membranes of present invention can be prepared by free radical co-polymerization of silicone material and other hydrophilic/hydrophobic moieties (see, e.g. FIG. 3). Typical silicone materials which are used in the invention are those which have multi —Si—O— repeat units and vinyl or acryl reactive functional end groups, which may also contain some other functional groups such as —OH, —NH$_2$, —COOH. The typical silicone materials used in this invention are mono vinyl terminated polydimethylsiloxane and mono methacryloxypropyl terminated polydimethylsiloxane (see FIG. 4). The typical hydrophilic moieties include all water-soluble materials containing vinyl or acryl reactive functional groups. FIG. 3 shows some illustrative hydrophilic moieties used in this invention such as 2-methacryloyloxyethyl phosphorylcholine, n-vinyl pyrrolidone, dihydroxypropyl methacrylate, dimethyl methacrylamide, 2-hydroxyethyl methacrylate, poly(ethylene glycol) methyl ether methacrylate, and mono ally mono trimethylsiloxy terminated polyethylene oxide. Typical hydrophobic materials used in this invention could be any non water-soluble moieties with vinyl or aryl reactive functional groups (FIG. 3). Common embodiments utilize methyl methacrylate, 2-phenylethyl acrylate and 4-phenylbutyl methacrylate.

B. Typical Combinations of Sensor Elements

Embodiments of the invention further include sensors comprising the blended polymeric compositions disclosed herein in combination with other sensor elements such as an interference rejection membrane (e.g. an interference rejection membrane as disclosed in U.S. patent application Ser. No. 12/572,087, the contents of which are incorporated by reference). One such embodiment of the invention is a interference rejection membrane comprising methacrylate polymers having a molecular weight between 100 and 1000 kilodaltons, wherein the methacrylate polymers are crosslinked by a hydrophilic crosslinking agent such as an organofunctional dipodal alkoxysilane. Another embodiment of the invention is a interference rejection membrane comprising primary amine polymers having a molecular weight between 4,000 Daltons and 500 kilodaltons, wherein the primary amine polymers are crosslinked by a hydrophilic crosslinking agent such as glutaraldehyde. Typically these interference rejection membrane coat a hydrogen peroxide transducing composition. In an illustrative embodiment, the hydrogen peroxide transducing composition comprises an electrode; and the crosslinked interference rejection membrane is coated on the electrode in a layer between 0.1 μm and 1.0 μm thick.

In some embodiments of the invention, an element of the sensor apparatus such as an electrode or an aperture is designed to have a specific configuration and/or is made from a specific material and/or is positioned relative to the other elements so as to facilitate a function of the sensor. In one such embodiment of the invention, a working electrode, a counter electrode and a reference electrode are positionally distributed on the base and/or the conductive layer in a configuration that facilitates sensor start up and/or maintains the hydration of the working electrode, the counter electrode and/or the reference electrode when the sensor apparatus is placed in contact with a fluid comprising the analyte (e.g. by inhibiting shadowing of an electrode, a phenomena which can inhibit hydration and capacitive start-up of a sensor circuit). Typically such embodiments of the invention facilitate sensor start-up and/or initialization.

Optionally embodiments of the apparatus comprise a plurality of working electrodes and/or counter electrodes and/or reference electrodes (e.g. 3 working electrodes, a reference electrode and a counter electrode), in order to, for example, provide redundant sensing capabilities. Certain embodiments of the invention comprising a single sensor. Other embodiments of the invention comprise multiple sensors. In some embodiments of the invention, a pulsed voltage is used to obtain a signal from one or more electrodes of a sensor. Optionally, the plurality of working, counter and reference electrodes are configured together as a unit and positionally distributed on the conductive layer in a repeating pattern of units. In certain embodiments of the invention, the elongated base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment.

In certain embodiments of the invention comprising multiple sensors, elements such as the sensor electrodes are organized/disposed within a flex-circuit assembly. In such embodiments of the invention, the architecture of the sensor system can be designed so that a first sensor does not influence a signal etc. generated by a second sensor (and vice versa); and so that the first and second sensors sense from separate tissue envelopes; so the signals from separate sensors do not interact. At the same time, in typical embodiments of the invention the sensors will be spaced at a distance from each other so that allows them to be easily packaged together and/or adapted to be implanted via a single insertion action. One such embodiment of the invention is an apparatus for monitoring an analyte in a patient, the apparatus comprising: a base element adapted to secure the apparatus to the patient; a first piercing member coupled to and extending from the base element; a first electrochemical sensor operatively coupled to the first piercing member and comprising a first electrochemical sensor electrode for determining at least one physiological characteristic of the patient at a first electrochemical sensor placement site; a second piercing member coupled to and extending from the base element; a second electrochemical sensor operatively coupled to the second piercing member and comprising a second electrochemical sensor electrode for determining at least one physiological characteristic of the patient at a second electrochemical sensor placement site. In such embodiments of the invention, at least one physiological characteristic monitored by the first or the second electrochemical sensor comprises a concentration of a naturally occurring analyte in the patient; the first piercing member disposes the first electrochemical sensor in a first tissue compartment of the patient and the second piercing member disposes the second electrochemical sensor in a second tissue compartment of the patient; and the first and second piercing members are disposed on the base in a configuration selected to avoid a physiological response that can result from implantation of the first electrochemical sensor from altering a sensor signal generated by the second electrochemical sensor.

In an embodiment of the invention that is designed to optimize electrode properties such as hydration, the working electrode, the counter electrode and the reference electrode are positionally distributed on conductive layer in a parallel configuration arranged so that a first electrode is disposed in a region on a first edge of the elongated base layer; a second electrode is disposed in a region on an opposite edge of the elongated base layer; and a third is disposed in a region of the elongated base layer that between the first electrode and the second electrode. Optionally, the working electrode, the counter electrode and the reference electrode are positionally distributed on conductive layer in a configuration arranged so that the working electrode is disposed in a region on a first edge of the elongated base layer; the counter electrode is disposed in a region on an opposite edge of the elongated base layer; and the reference electrode is disposed in a region of the elongated base layer that between the working electrode and the counter electrode. In certain embodiments of the invention, an edge or center of a reference electrode is lined up with an edge or center of the working or counter electrode. In other embodiments of the invention, an edge or center of a reference electrode is offset with an edge or center of the working or counter electrode. In some embodiments of the invention, an electrode matrix is formed in the sensor so as to have no side walls in a manner that further improve hydration of the sensor electrodes. Related embodiments of the invention include methods for using a distributed electrode configuration to facilitate and maintain the hydration and/or initialization properties of various sensor embodiments of the invention.

In some embodiments of the invention, one or more apertures is positioned on the cover layer so that a fluid comprising the analyte contacts the reference electrode, the working electrode and the counter electrode in a sequential manner so as to facilitate sensor hydration and/or sensor start-up or initialization. In other embodiments of the invention, the aperture is positioned on the cover layer directly over the reference electrode, the working electrode and the counter electrode so as to facilitate the hydration of these electrode proceeding equivalently. The cover layer can be constructed from a variety of materials know in the art and can include a variety of apertures having similar or dissimilar sizes, shapes and configurations. In some embodiments of the invention, the cover layer comprises a plurality of apertures (e.g. disposed in a row over the various sensor electrodes) and is formed from a sheath or tube made for example from a biocompatible polymeric material. Related embodiments of the invention include methods for using a specific aperture configuration to facilitate a property (e.g. initialization and/or start-up) of various sensor embodiments of the invention.

Various elements of the sensor apparatus can be disposed at a certain location in the apparatus and/or configured in a certain shape and/or be constructed from a specific material so as to facilitate strength and/or function of the sensor. One embodiment of the invention includes an elongated base comprised of a polyimmide or dielectric ceramic material that facilitates the strength and durability of the sensor. In certain embodiments of the invention, the structural features and/or relative position of the working and/or counter and/or reference electrodes is designed to influence sensor manufacture, use and/or function. Optionally, the sensor is operatively coupled to a constellation of elements that comprise a flex-circuit (e.g. electrodes, electrical conduits, contact pads and the like). One embodiment of the invention includes electrodes having one or more rounded edges so as to inhibit delamination of a layer disposed on the electrode (e.g. an analyte sensing layer comprising glucose oxidase). Related embodiments of the invention include methods for inhibiting delamination of a sensor layer using a sensor embodiments of the invention (e.g. one having one or more electrodes having one or more rounded edges). In some embodiments of the invention, a barrier element is disposed on the apparatus so as to inhibit spreading of a layer of material (e.g. an enzyme such as glucose oxidase) disposed on an electrode. Related embodiments of the invention include methods for inhibiting movement of a compound disposed on a sensor embodiments of the invention (e.g. one constructed to have such a barrier structure). Optionally, a barrier element is disposed on the apparatus so as to encircle a reactive surface of an electrode.

In certain embodiments of the invention, an electrode of the apparatus comprises a platinum composition and the apparatus further comprises a titanium composition disposed between the elongated base layer and the conductive layer. Optionally in such embodiments, apparatus further comprises a gold composition disposed between the titanium composition and the conductive layer. Such embodiments of the invention typically exhibit enhanced bonding between layered materials within the sensor and/or less corrosion and/or improved biocompatibility profiles. Related embodiments of the invention include methods for inhibiting corrosion of a sensor element and/or method for improving the biocompatibility of a sensor embodiments of the invention (e.g. one constructed to use such materials).

In typical embodiments of the invention, the sensor is operatively coupled to further elements (e.g. electronic components) such as elements designed to transmit and/or receive a signal, monitors, processors and the like as well as devices that can use sensor data to modulate a patient's physiology such as medication infusion pumps. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase and at least one working electrode is not coated with an analyte sensing layer comprising glucose oxidase.

C. Diagrammatic Illustration of Typical Sensor Configurations

Figure 2B:
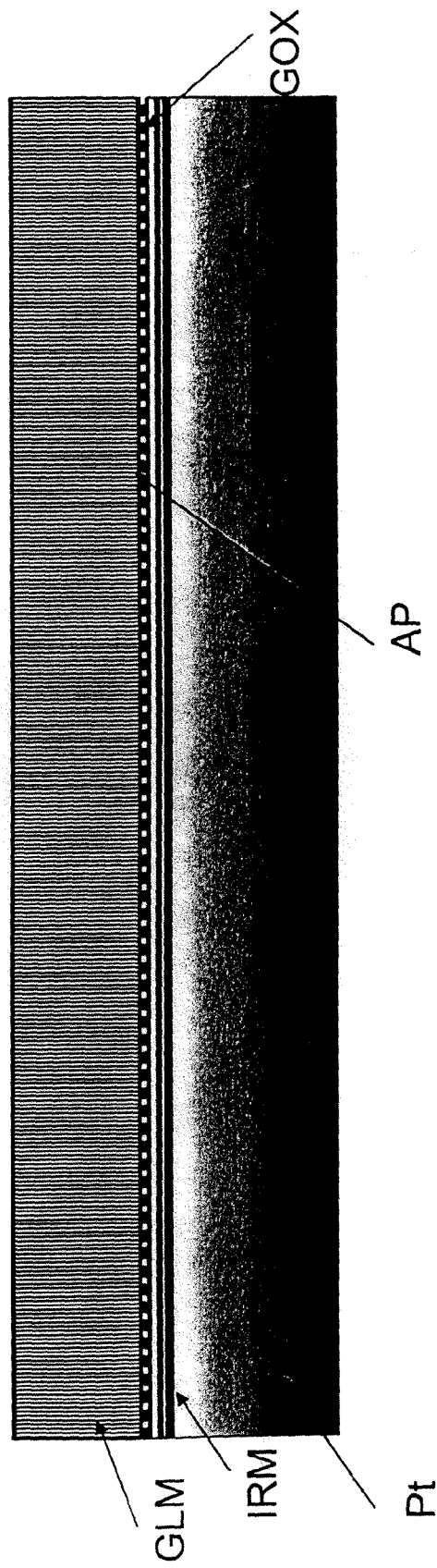
FIG. 2B provides a diagrammatic view of one embodiment of an amperometric analyte sensor having an interference rejection membrane.
Figure 3A:
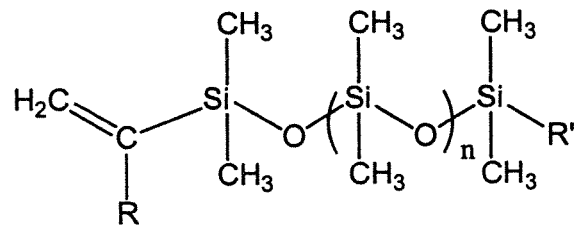
FIG. 3A shows exemplary silicone materials for use with the blended polymer embodiments of the invention.
Figure 3A:
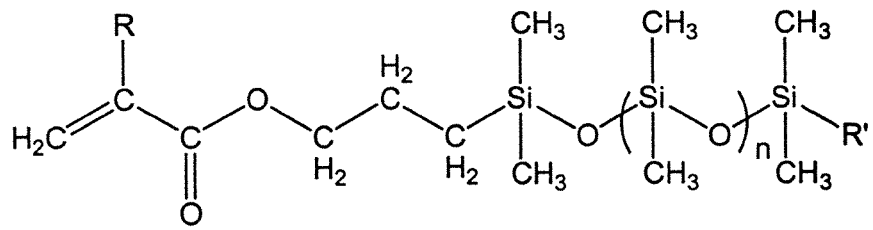
Figure 3B:
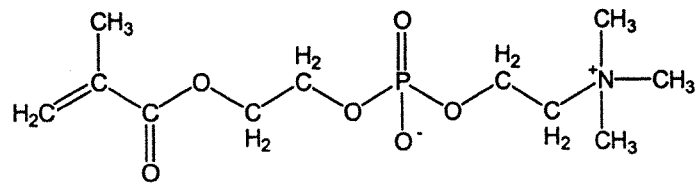
FIG. 3B shows exemplary hydrophilic materials for use with the blended polymer embodiments of the invention.
Figure 3B:
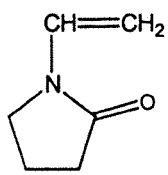
Figure 3B:
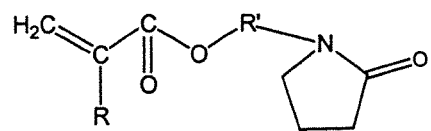
Figure 3B:
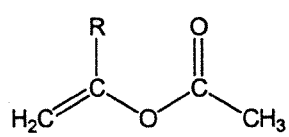
Figure 3B:
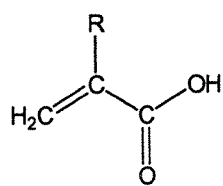
Figure 3B:
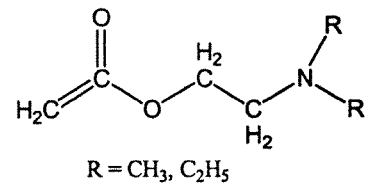
Figure 3B:
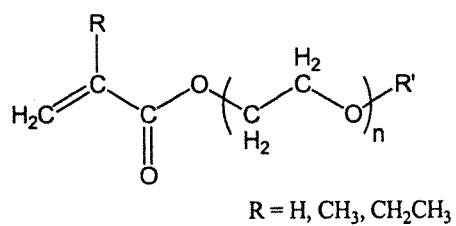
Figure 3C:
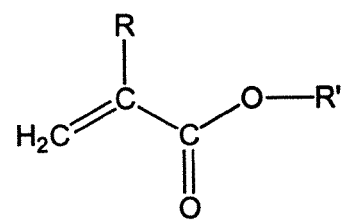
FIG. 3C shows exemplary hydrophobic materials for use with the blended polymer embodiments of the invention.

FIG. 2A illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2A includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2A, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 2B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns ($\mu$m) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like.

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels, the polymer blends disclosed herein or any other suitable hydrophilic membranes known to those skilled in the art.

In some embodiments of the invention, an adhesion promoter layer 114 is disposed between layers such as the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

D. Typical Analyte Sensor Constitutents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2A, the base constituent 102 comprises a ceramic. Alternatively, the base constituent comprises a polymeric material such as a polyimmide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 2A). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic crosslinked pHEMA and polylysine polymers as well as cellulose acetate (including cellulose acetate incorporating agents such as poly(ethylene glycol)), polyethersulfones, polytetra-fluoroethylenes, the perfluoronated ionomer NAFION, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference. Additional compositions having an unexpected constellation of material properties that make them ideal for use as interference rejection membranes in certain amperometric glucose sensors as well as methods for making and using them are disclosed herein, for example in U.S. patent application Ser. No. 12/572,087.

Analyte Sensing Constituent

The electrochemical sensors of the invention include an analyte sensing constituent disposed on the electrodes of the sensor (see, e.g. element 110 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent (see, e.g. element 116 in FIG. 2A). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2A). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase ($GO_x$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In typical embodiments of the invention, the analyte modulating composition includes the blended polymeric compositions disclosed herein.

Cover Constituent

The electrochemical sensors of the invention include one or more cover constituents which are typically electrically insulating protective constituents (see, e.g. element 106 in FIG. 2A). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

E. Illustrative Embodiments of Analyte Sensor Apparatus and Associated Characteristics The analyte sensor apparatus disclosed herein has a number of embodiments. A general embodiment of the invention is an analyte sensor apparatus for implantation within a mammal. While the analyte sensors are typically designed to be implantable within the body of a mammal, the sensors are not limited to any particular environment and can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include, for example, those used to monitor one or more analytes present in one or more physiological environments in a hospitalized patient.

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example, in such implanted oxygen sensor apparatus designs, oxygen noise at the reference sensor can compromise the signal to noise ratio which consequently perturbs their ability to obtain stable glucose readings in this environment. The peroxide sensors of the invention therefore overcome the difficulties observed with such oxygen sensors in non-vascular regions.

Certain peroxide sensor embodiments of the invention further include advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors described herein can be categorized into three groups based on implant duration: (1) "Limited" (<24 hours), (2) "Prolonged" (24 hours-30 days), and (3) "Permanent" (>30 days). In some embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

In general, the analyte sensor apparatus structure comprises a base layer and a conductive layer disposed upon the base layer and comprises one or more electrodes. For example, the conductive layer can include a working electrode, a reference electrode and/or a counter electrode. These electrodes can be spaced in proximity, or alternatively are spaced distally, according to the specific design. The sensor apparatus design is such that certain electrodes (e.g. the working electrode) can be exposed to the solution containing the analyte to be sensed (e.g. via an aperture) in the sensor apparatus. The sensor apparatus design is such that certain electrodes (e.g. the reference electrode) are not exposed to the solution containing the analyte to be sensed in the sensor apparatus.

Typically, the analyte sensor apparatus includes an analyte sensing layer disposed on a conductive layer of the sensor, typically covering a portion or all of the working electrode. This analyte sensing layer detectably alters the electrical current at the working electrode in the conductive layer in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers comprise an enzyme such as glucose oxidase (e.g. for use in glucose sensors) or lactate oxidase (e.g. for use in lactate sensors). In some embodiments of the invention, the analyte sensing layer is disposed upon a porous metallic and/or ceramic and/or polymeric matrix with this combination of elements functioning as an electrode in the sensor.

Typically, the analyte-sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin, for example, less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings described herein, these thin coatings are typical embodiments of the invention.

Optionally, the analyte sensing layer has a protein layer disposed thereon and which is typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function and provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as GOx from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Optionally, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layers exhibit unexpected properties including an enhanced overall stability. In addition, silane containing adhesion promoting layers provide a number of advantageous characteristics in addition to an ability to enhancing sensor stability, and can, for example, play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serve to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. In certain embodiments of the invention, the analyte modulating layer comprises a linear polyurethane/polyurea polymer blended with a branched acrylate hydrophilic comb-copolymer having a central chain and a plurality of side chains coupled to the central chain, wherein at least one side chain comprises a silicone moiety.

Typically the analyte modulating layer further comprises one or more cover layers which are typically electrically insulating protective layers disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. An illustrative cover layer comprises spun on silicone. Typically the cover layer further includes an aperture that exposes at least a portion of a sensor layer (e.g. analyte modulating layer) to a solution comprising the analyte to be sensed.

The analyte sensors described herein can be polarized cathodically to detect, for example, changes in current at the working cathode that result from the changes in oxygen concentration proximal to the working cathode that occur as glucose interacts with glucose oxidase as shown in FIG. 1. Alternatively, the analyte sensors described herein can be polarized anodically to detect for example, changes in current at the working anode that result from the changes in hydrogen peroxide concentration proximal to the working anode that occur as glucose interacts with glucose oxidase as shown in FIG. 1. In typical embodiments of the invention, the current at the working electrode(s) is compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

A specific illustrative example of an analyte sensor apparatus for implantation within a mammal is a peroxide sensor of the following design. A first layer of the peroxide sensor apparatus is a base layer, typically made from a ceramic such as alumina. A subsequent layer disposed upon the base layer is a conductive layer including a plurality of electrodes including an anodic working electrode and a reference electrode. A subsequent layer disposed on the conductive layer is an analyte sensing layer that includes crosslinked glucose oxidase which senses glucose and consequently generates hydrogen peroxide as shown in FIG. 1. In the presence of this hydrogen peroxide, the anodic working electrode experiences a measurable increase in current as the hydrogen peroxide generated contacts this anode in the conductive layer and is oxidized. The reference electrode serves as a control and is physically isolated from the working electrode and the hydrogen peroxide generated according to the reaction shown in FIG. 1. This analyte sensing layer is typically less than 1, 0.5, 0.25 or 0.1 microns in thickness and comprises a mixture of crosslinked human serum albumin in a substantially fixed ratio with the crosslinked glucose oxidase, with the glucose oxidase and the human serum albumin being distributed in a substantially uniform manner throughout the sensor layer. An optional subsequent layer disposed on the sensor layer is a protein layer comprising crosslinked human serum albumin. An optional subsequent layer disposed on the lower layer is an adhesion promoting layer which promotes the adhesion between the analyte sensing layer and/or the protein layer and an analyte modulating layer which is disposed upon these layers. This adhesion promoting layer comprises a silane composition. A subsequent layer disposed on the adhesion promoting layer is the analyte modulating layer in the form of a hydrophilic glucose limiting membrane comprising PDMS which modulates the diffusion of glucose therethrough. In certain embodiments of the invention, the analyte modulating layer comprises a linear polyurethane/polyurea polymer blended with a branched acrylate copolymer having a central chain and a plurality of side chains coupled to the central chain, wherein at least one side chain comprises a silicone moiety. A subsequent layer is a cover layer, typically composed of silicone, which is disposed on at least a portion of the analyte modulating layer, wherein the cover layer further includes an aperture that exposes at least a portion of the analyte modulating layer to the external glucose containing environment so that the glucose can access the analyte sensing layer on the working electrode.

F. Permutations of Analyte Sensor Apparatus and Elements

As noted above, the invention disclosed herein includes a number of embodiments including sensors having constellations of elements including blended polymeric membranes. Such embodiments of the invention allow artisans to generate a variety of permutations of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of the invention is shown in FIG. 2. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 2 the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imageable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photo-resist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize a separate reference element not formed on the sensor. The exposed electrodes and/or contact pads can also undergo secondary processing through the apertures 108, such as additional plating processing, to prepare the surfaces and/or strengthen the conductive regions.

An analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. Typically the sensor chemistry layer 110 is disposed on portions of a working electrode and a counter electrode that comprise a conductive layer. Some methods for generating the thin sensor chemistry layer 110 include spin coating processes, dip and dry processes, low shear spraying processes, ink-jet printing processes, silk screen processes and the like. Most typically the thin sensor chemistry layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. In certain embodiments of the invention, the analyte modulating layer comprises a linear polyurethane/polyurea polymer blended with a branched acrylate hydrophilic comb-copolymer having a central chain and a plurality of side chains coupled to the central chain, wherein at least one side chain comprises a silicone moiety.

In some embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including an UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming an UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

The sensors of the invention can have any desired configuration, for example planar or cylindrical. The base layer 102 can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements and coating layers are continuously applied.

A general embodiment of the invention is a sensor designed for implantation within a body that comprises a base layer, an analyte sensing layer disposed upon the base layer which includes a plurality of sensor elements, an enzyme layer (typically less than 2 microns in thickness) disposed upon the analyte sensing layer which coats all of the plurality of sensing elements on the conductive layer, and one or more coating layers. Typically the enzyme layer comprises glucose oxidase; typically in a substantially fixed ratio with a carrier protein. In a specific embodiment, the glucose oxidase and the carrier protein are distributed in a substantially uniform manner throughout the disposed enzyme layer. Typically the carrier protein comprises albumin, typically in an amount of about 5% by weight. As used herein, "albumin" refers to those albumin proteins typically used by artisans to stabilize polypeptide compositions such as human serum albumin, bovine serum albumin and the like. In some embodiments of the invention, a coating layer is an analyte contacting layer which is disposed on the sensor so as to regulate the amount of analyte that can contact the enzyme layer. In further embodiments, the sensor includes an adhesion promoter layer disposed between the enzyme layer and the analyte contacting layer; and, the enzyme layer is less than 1, 0.5, 0.25 or 0.1 microns in thickness.

Embodiments of the invention include a design where an analyte sensing layer is disposed upon a porous metallic and/or ceramic and/or polymeric matrix with this combination of elements functioning as an electrode in the sensor. A related embodiment of the invention is an electrochemical analyte sensor which includes a base layer, a conductive layer disposed upon the base layer that includes at least one working electrode and at least one counter electrode, an analyte sensing layer disposed upon the conductive layer, wherein the analyte sensing layer is less than 2 microns in thickness; and an analyte modulating layer that regulates the amount of analyte that contacts the enzyme layer, typically by limiting the amount of analyte that can diffuse through the layer and contact the analyte sensing layer. In certain embodiments of the invention, the analyte modulating layer comprises a linear polyurethane/polyurea polymer blended with a branched acrylate comb-copolymer having a central chain and a plurality of side chains coupled to the central chain, wherein at least one side chain comprises a silicone moiety. In an optional embodiment of the invention, the working electrode and/or the coated surface of the working electrode is larger than counter electrode and/or the coated surface of the counter electrode. In some embodiments, the enzyme layer comprises glucose oxidase stabilized by coating it on the working electrode and the counter electrode in combination with a carrier protein in a fixed ratio. In one embodiment, this glucose oxidase enzyme layer substantially covers the conductive layer. Embodiments where the glucose oxidase enzyme layer is disposed in a uniform coating over the whole conductive layer are typical because they may avoid problems associated with sensors having multiple different coatings on a single layer such as the selective delamination of different coatings having different material properties. Typically, the sensor includes an adhesion promoting layer disposed between the enzyme layer and the analyte modulating layer.

G. Analyte Sensor Apparatus Configurations

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

FIG. 2 provides a diagrammatic view of a typical analyte sensor configuration of the current invention. Certain sensor configurations are of a relatively flat "ribbon" type configuration that can be made with the analyte sensor apparatus. Such "ribbon" type configurations illustrate an advantage of the sensors disclosed herein that arises due to the spin coating of sensing enzymes such as glucose oxidase, a manufacturing step that produces extremely thin enzyme coatings that allow for the design and production of highly flexible sensor geometries. Such thin enzyme coated sensors provide further advantages such as allowing for a smaller sensor area while maintaining sensor sensitivity, a highly desirable feature for implantable devices (e.g. smaller devices are easier to implant). Consequently, sensor embodiments of the invention that utilize very thin analyte sensing layers that can be formed by processes such as spin coating can have a wider range of geometrical configurations (e.g. planar) than those sensors that utilize enzyme layers formed via processes such as electrodeposition.

Certain sensor configurations include multiple conductive elements such as multiple working, counter and reference electrodes. Advantages of such configurations include increased surface area which provides for greater sensor sensitivity. For example, one sensor configuration introduces a third working sensor. One obvious advantage of such a configuration is signal averaging of three sensors which increases sensor accuracy. Other advantages include the ability to measure multiple analytes. In particular, analyte sensor configurations that include electrodes in this arrangement (e.g. multiple working, counter and reference electrodes) can be incorporated into multiple analyte sensors. The measurement of multiple analytes such as oxygen, hydrogen peroxide, glucose, lactate, potassium, calcium, and any other physiologically relevant substance/analyte provides a number of advantages, for example the ability of such sensors to provide a linear response as well as ease in calibration and/or recalibration.

An exemplary multiple sensor device comprises a single device having a first sensor which is polarized cathodically and designed to measure the changes in oxygen concentration that occur at the working electrode (a cathode) as a result of glucose interacting with glucose oxidase; and a second sensor which is polarized anodically and designed to measure changes in hydrogen peroxide concentration that occurs at the working electrode (an anode) as a result of glucose coming form the external environment and interacting with glucose oxidase. As is known in the art, in such designs, the first oxygen sensor will typically experience a decrease in current at the working electrode as oxygen contacts the sensor while the second hydrogen peroxide sensor will typically experience an increase in current at the working electrode as the hydrogen peroxide generated as shown in FIG. 1 contacts the sensor. In addition, as is known in the art, an observation of the change in current that occurs at the working electrodes as compared to the reference electrodes in the respective sensor systems correlates to the change in concentration of the oxygen and hydrogen peroxide molecules which can then be correlated to the concentration of the glucose in the external environment (e.g. the body of the mammal).

The analyte sensors of the invention can be coupled with other medical devices such as medication infusion pumps. In an illustrative variation of this scheme, replaceable analyte sensors of the invention can be coupled with other medical devices such as medication infusion pumps, for example by the use of a port couple to the medical device (e.g. a subcutaneous port with a locking electrical connection).

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; U.S. Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a linear polyurethane/polyurea polymer blended with a branched acrylate copolymer having a central chain and a plurality of side chains coupled to the central chain. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including chemical vapor deposition, physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a sensor chemistry enzyme layer can then be disposed on the sensing layer by electrochemical deposition or a method other than electrochemical deposition such a spin coating, followed by vapor crosslinking, for example with a dialdehyde (glutaraldehyde) or a carbodi-imide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Subsequent to treatment of the sensor elements, one or more additional functional coatings or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as exact the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt % Among the copolymers listed above, the dimethylsiloxane-bisphenol A carbonate copolymer which comprises 50-55 wt % of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane nonsiloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, the cover layer that is added to the glucose sensors of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a linear polyurethane/polyurea polymer blended with a branched acrylate copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a sensor chemistry layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Methods for Using Analyte Sensor Apparatus of the Invention

A related embodiment of the invention is a method of sensing an analyte within the body of a mammal, the method comprising implanting an analyte sensor embodiment disclosed herein in to the mammal and then sensing an alteration in current at the working electrode and correlating the alteration in current with the presence of the analyte, so that the analyte is sensed. The analyte sensor can polarized anodically such that the working electrode where the alteration in current is sensed is an anode, or cathodically such that the working electrode where the alteration in current is sensed is an cathode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

An exemplary kit comprises a container and, within the container, an analyte sensor apparatus comprising a base layer; a conductive layer disposed upon the base layer; wherein the conductive layer includes a working electrode an analyte sensing layer disposed on the conductive layer; wherein the analyte sensing layer detectably alters the electrical current at the working electrode in the conductive layer in the presence of an analyte; an analyte modulating layer disposed on the analyte sensing layer, wherein the analyte modulating layer modulates the diffusion of the analyte therethrough; the analyte modulating layer comprising a blend of a linear polyurethane/polyurea copolymer and a branched acrylate copolymer having a central chain and a plurality of side chains coupled to the central chain, wherein at least one side chain comprises a silicone moiety; and instructions for using the analyte sensor apparatus.

Various publication citations are referenced throughout the specification. In addition, certain text from related art is reproduced herein to more clearly delineate the various embodiments of the invention. The disclosures of all citations in the specification are expressly incorporated herein by reference.

EXAMPLES

The following examples are given to aid in understanding the invention, but it is to be understood that the invention is not limited to the particular materials or procedures of examples. All materials used in the examples were obtained from commercial sources.

Example 1

Synthesis and Characterization of Illustrative Linear Polyurea/Polyurethane Polymers The disclosure provided herein in combination with what is known in that art confirms that functional linear polyurethane/polyurea polymers can be made from a number of formulations, for example those disclosed in U.S. Pat. Nos. 5,777,060; 5,882,494; 6,642,015; and PCT publications WO 96/30431; WO 96/18115; WO 98/13685; and WO 98/17995, the contents of which are incorporated herein by reference. Certain of these polymers provide formulations useful as a glucose limiting membrane (GLM).

A standard GLM formulation used to make embodiments of the invention comprises:

25 mol % polymethylhydrosiloxane (PDMS), trimethylsilyl terminated, 25-35 centistokes;

75 mol % polypropylene glycol diamine (Jeffamine 600, a polyoxyalkyleneamine with an approximate molecular weight of 600); and 50 mol % of a diisocyanate (e.g., 4,4'-diisocyanate).

This standard GLM formulation and processes for its synthesis are disclosed for example in U.S. Pat. Nos. 6,642,015, 5,777,060 and 6,642,015.

Another formulation used in embodiments of the invention is termed a "half permeable GLM", due to the observation that its glucose permeability is one-half of the standard formulation immediately above. In the standard GLM, the Jeffamine/PDMS ration=3/1 (mole ratio). In contrast, in the "half permeable GLM", this ratio is altered so that the Jeffamine/PDMS=12/1. This half-permeable GLM is can be used for example to reduce the weight % of GLM-urea in an overall polymer blend in order to reach a particular Isig (or glucose permeability). Also, the presence of more GLM-acrylate polymer in the polymer blend can enhance the adhesion between blended polymeric membrane layer and a proximal layer in a sensor (e.g. one comprising glucose oxidase).

Example 2

Synthesis and Characterization of Illustrative Branched Acrylate Polymers

The disclosure provided herein in combination with what is known in that art confirms that functional branched acrylate can be made from a number of formulations. In one example, the formulation is made using 9.60 g (40%) MMA (methyl methacrylate, Mw 100.12 Daltons); 8.40 g (35%) PDMS-M11 (polydimethyl siloxane monomethacryloxypropyl, Mw=1000 Daltons); 2.40 (10%) methoxy-PEO-MA (poly (ethylene oxide)methyl ether methacrylate, Mw=1100 Daltons); and 3.60 (15%) 2-DMA-EMA (2-(Dimethylamino) ethyl methacrylate, Mw 157 Daltons)

TABLE A

Other branched acrylate formulations can be made with the following constituents:

| Batch # | wt % of 2-DMA-EMA | wt % of MMA | wt % of PDMS-M11 | wt % of PEO-MA |
|---|---|---|---|---|
| 2843-4-1B | 5 | 45 | 35 | 15 |
| 2843-4-2B | 48 | 0 | 35 | 17 |

TABLE A-continued

Other branched acrylate formulations can be made with the following constituents:

| Batch # | wt % of 2-DMA-EMA | wt % of MMA | wt % of PDMS-M11 | wt % of PEO-MA |
|---|---|---|---|---|
| 2843-28-1 | 25 | 20 | 45 | 10 |
| 2843-30-2 | 35 | 20 | 40 | 5 |

2-DMA-EMA = 2-(dimethylamino) ethyl methacrylate
MMA = Methyl methacrylate
PDMS-M11 = polydimethyl siloxane monomethacryloxypropyl
PEO-MA = poly(ethylene oxide) methyl ether methacrylate

TABLE B other branched acrylate formulations can be made with the following conditions and constituents:

| GLM Lot # | % MMA | % PDMS-M11 | % methoxy-PEO-MA | % HEMA | 2-DMA-EMA | AIBN (mg) | Solvent (ml) | RXN Time (hrs) |
|---|---|---|---|---|---|---|---|---|
| 3276-66-2 | 34 | 33 | 18 | 5 | 10 | 50 | 60 THF | 24.0 |
| 3276-93-1 | 20 | 35 | 10 | | 35 | 200 | 240 THF | 24.0 |

HEMA = 2-hydroxyethyl methacrylate (Mw 130.14 Daltons)
AIBN = Azobisisobutyronitrile (Mw = 164.21 Daltons)

Illustrative Synthesis Scheme for a Branched Acrylate Polymer:

9.6 g polydimethyl siloxane monomethacrylate (Mw=1000), 4.08 g methoxy poly(ethylene oxide) monomethacrylate (Mw=1000), 10.32 g methyl methacrylate, 50 mg 2,2'-azobisisobutyronitrile and 60 ml ethoxy ethyl acetate were added into a 200 mL round bottom flask containing a magnetic stirring bar. All chemicals were mixed together by Stirring for 20 min. Made two-time freeze-vacuum-thaw-nitrogen for mixture to remove all oxygen in the round bottle flask.

The flask was placed into one oil bath. The solution was then heated to 75° C. After 16-24 h, the bottle was removed from the oil batch and allowed to cool down to room temperature.

The polymer solution was precipitated into 1000 ml of DI water and filtered out, then dissolved in 100 ml of THF again, and precipitated into 1000 ml $H_2O$.

The solid polymer was filtered out and dried at 70° C. until constant weight.

Another Illustrative Synthesis Scheme for a Branched Acrylate Polymer 7.2 g polydimethyl siloxane monomethacrylate (Mw=1000), 7.2 g vinyl pyrolidone, 9.6 g methyl methacrylate, 50 mg 2,2'-azobisisobutyronitrile and 60 ml THF were added into a 200 mL round bottom flask containing a magnetic stirring bar. All chemical were mixed together by Stirring for 20 min.

Made two-time freeze-vacuum-thaw-nitrogen for mixture to remove all oxygen in the round bottle flask.

The flask was placed into one oil bath. The solution was then heated to 75° C. After 16-24 h, the bottle was removed from the oil batch and allowed to cool down to room temperature.

The polymer solution was precipitated into 1000 ml of DI water, dissolved in 100 ml of THF again and precipitated into 1000 ml $H_2O$.

The solid polymer was filtered out and dried at 70° C. until constant weight.

More representative silicone based comb-copolymer formulations made by the above procedures are listed in Table 1.

Characterization of Branched Acrylate Polymers a). Molecular weights of comb-copolymers were determined by Gel Permeation Chromatography (Waters, Inc) using THF/acetic acid (95:5 v/v) as mobile phase. Monodisperse Polystyrene standards were used for calibration. All data are showed in Table 2.

b). Infrared spectra of comb-copolymers were obtained using Nicolet Nexus 670 FT-IR. FIG. 7 shows the spectrum of sample #5 listed in Table 1, exhibiting the expected absorbance band ($cm^{-1}$).

c). Water uptake was determined gravimetrically at room temperature on films which were less then 0.5 mm thick. After evaporation of casting solvent, films were dried to constant weight at 50° C. in vacuum oven, weighted, immersed in deionzed water for 24 h, removed and blotted with filter paper, and weighted. Percent water uptake was determined from the formula:

$$\text{uptake} = [(W_w - W_d)/W_d] \times 100$$

Where $W_w$ is the weight of the swollen film and $W_d$ is the weight of the dry film. The results are shown in Table 2.

d). Diffusion constants were measured in a standard diffusion cell (Crown Glass Co. Inc.) maintained at 37° C. using Fick's relationship:

$$J = D \, dC/dx$$

Where J is total flux, D is the diffusion constant, and dC/dx is the concentration gradient across the membrane.

Glucose diffusion constant ($D_G$) was determined by securing the membrane with two rubber gasket between the two halves of a diffusion cell maintained at 37° C. One side was filled with 2400 mg/dL glucose in phosphate buffered saline (PBS, 0.15M NaCl, 0.05M phosphate, PH=7.4), the other side was filled with phosphate buffered saline. The concentration of glucose in each half of the cell was measured at appropriate intervals using a YSI glucose analyzer. The curve of concentration vs. time was plotted and the diffusion constant was calculated. Results are shown in Table 2.

Oxygen diffusion constant ($D_o$) was determined using the same diffusion cell. Each side of the cell was filled with phosphate buffered saline. One side was saturated with high purity $O_2$, the other side was saturated with high purity $N_2$. Two calibrated oxygen electrodes were placed in two cells and oxygen concentration from both cells were recorded as a function of time. The curve of oxygen concentration vs. time was plotted and the constant was calculated. Curve generally had correlation coefficients ($R^2$) of greater than 0.99. All data are set forth in Table 2.

Sensor Preparation Using Branched Acrylate Polymer Alone and Sensor Performance in In-Vitro and In-Vivo Testing:

a). The silicone-based comb-copolymer was evaluated using a prototype glucose sensor. A sensor was constructed having a reference electrode, a working electrode, and a counter electrode deposited on a polyimide sheet. The electrodes were covered with a layer of cross-linked glucose oxidase and then coated with a layer of silicone-based comb-copolymer by spray coating of comb-copolymer solution in THF.

b). Glucose response in in-vitro (comb-copolymer #5 in Table 1 is used in this example). The response of the electrode system was close to linear relationship over the physiological glucose range. The sensor didn't show oxygen effect even at very low oxygen level (2%).

c). In-vivo testing result (made from comb-copolymer #5 in Table 1) shows sensor with new comb-copolymer tracks blood glucose level very well in a canine model.

Example 3

Synthesis and Characterization of Illustrative Blended Polymeric Compositions

Figure 5:
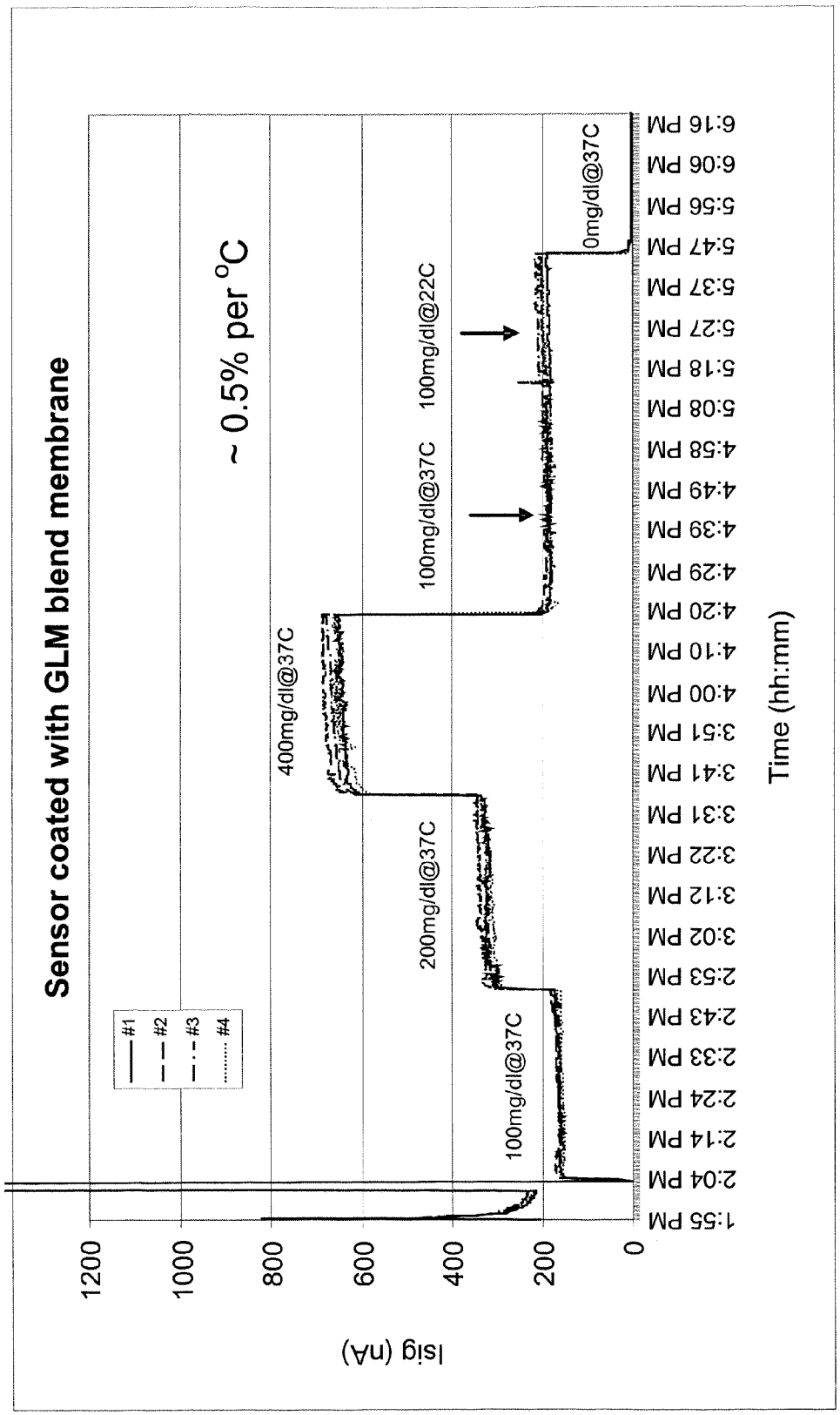
FIG. 5 illustrates how glucose sensors comprising an analyte modulating membrane made from a branched acrylate polymer blended with a linear polyurethane/polyurea polymer exhibit a stabilized glucose permeability over a range of temperatures. Specifically as the polyurethane/polyurea polymer and the branched acrylate polymer have opposite slopes for glucose permeability vs. temperature plots, the blended membrane successfully balances the temperature dependency of two different polymeric compositions. Therefore, the glucose sensor coated with a blended polymeric composition is much less sensitive to the environmental temperature changes than sensors coated with a linear polyurethane/polyurea polymer alone. This property will for example increase the accuracy of glucose sensor over a range of temperatures. The glucose sensor in FIG. 5 only showed very little change (~0.5% per C) on its Isig (electronic signal reading from the sensor) when it was transferred from 100 mg/dl glucose solution at 37° C. to 100 mg/dl glucose solution at 22° C.
Figure 6A:
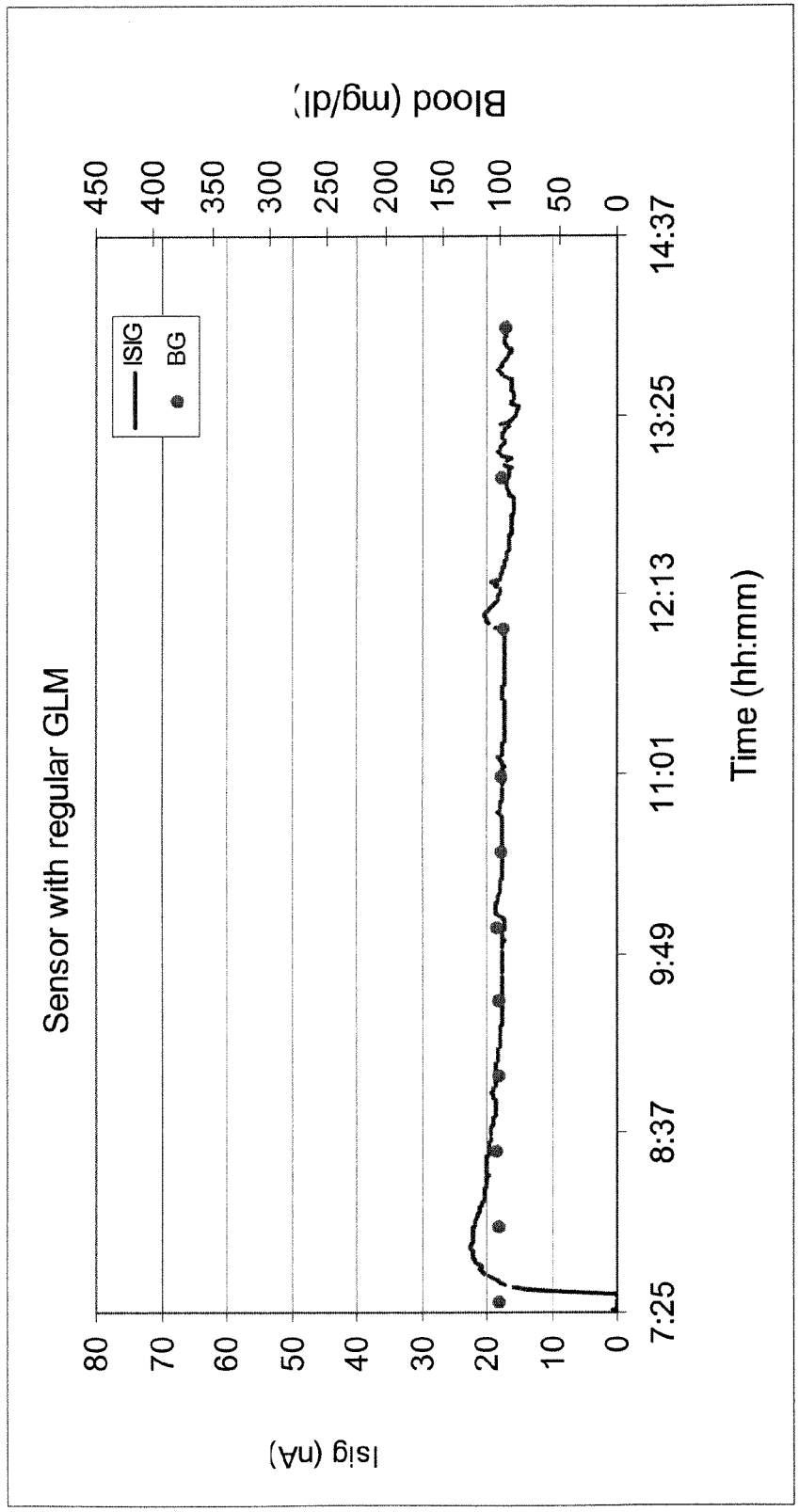
FIGS. 6A and 6B provide data showing that glucose sensors coated with a blended polymeric composition have a faster run-in than sensors coated with a linear polyurethane/polyurea polymer alone in vivo (in a canine model). In these charts, the difference is about 2 minutes (blended composition) vs. 7 minutes (linear polyurethane/polyurea polymer). This data shows that glucose sensors comprising an analyte modulating membrane made from a branched acrylate polymer blended with a linear polyurethane/polyurea polymer hydrate and stabilize very fast (fast run-in or break-in time). Consequently, such sensors can report the glucose signal almost immediately after the sensor is inserted into an in vivo environment.
Figure 6B:
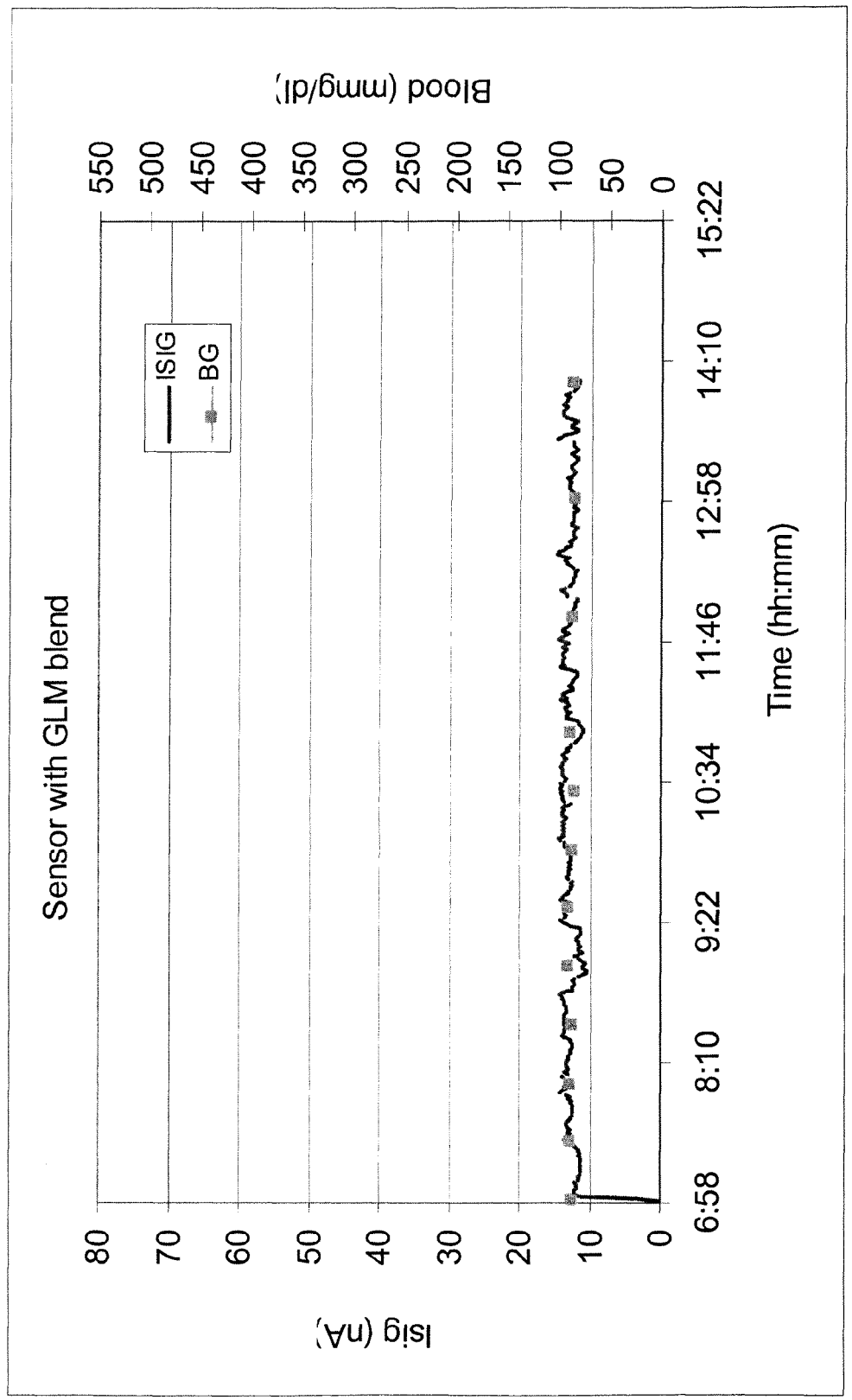

The linear polyurethane/polyurea polymer used to make blended membrane composition embodiments of the invention comprised the "standard GLM" formulation shown in Example 1 above. The branched acrylate polymer ("GLM-acrylate") used to make blended membrane compositions of the invention comprised the formulation of lot #3276-66-2 shown in Table B in Example 2 above. For the sensors comprising blended membranes that were produced and then used to generate the data as shown in FIGS. 4-6, the GLM/GLM-acrylate ratio=1/1 (by weight).

Art accepted processes were used for making the polymer blends. Basically, amounts of standard GLM and GLM-acrylate polymer were dissolved in THF (or THF/IPA) for few hours, then filtered with 1 micron filter before use according to standard methods for making a layered sensor. For example, the common concentration for spraying processes was 2-3% solid, and for spinning processes was 6-8% solid.

Tables

TABLE 1

SYNTHESIS OF BRANCHED ACRYLATE COPOLYMERS

| # | PDMS-MA (wt %) | PEO-MA (wt %) | VP (wt %) | MMA (wt %) |
|---|---|---|---|---|
| 1 (2213-37-1) | 30% | 25% | 0% | 45% |
| 2 (2213-47-1) | 30% | 25% | 0% | 50% |
| 3 (2213-54-1) | 30% | 18% | 0% | 52% |
| 4 (2213-56-2) | 35% | 18% | 0% | 47% |
| 5 (2151-57) | 35% | 17% | 0% | 48% |
| 6 | 40% | 17% | 0% | 43% |
| 7 (2151-58) | 35% | 16% | 0% | 49% |
| 8 (2213-47-2) | 30% | 15% | 0% | 55% |
| 9 (2213-54-2) | 50% | 20% | 0% | 30% |
| 10 (2213-56-1) | 40% | 18% | 0% | 42% |
| 11 (2213-59-2) | 30% | 0% | 30% | 40% |

PDMA-MA: polydimethyl siloxane monomethacrylate (Mw is about 1000 g/mol)
PEO-MA: poly(ethylene oxide) methyl ether methacrylate (Mw is about 1000 g/mol)
VP: n-vinyl pyrrolidone
MMA: methyl methacrylate

TABLE 2

CHARACTERIZATION OF BRANCHED ACRYLATE COPOLYMERS

| # | Mw (kg/mol) | Glucose diffusion constant ($cm^2/s$) | $O_2$ diffusion constant ($cm^2/s$) | Water Uptake (%) |
|---|---|---|---|---|
| 1 (2213-37-1) | 161 | $140 \times 10^{-9}$ | $1.30 \times 10^{-5}$ | 40 |
| 2 (2213-47-1) | 167 | $22 \times 10^{-9}$ | $1.10 \times 10^{-5}$ | 20 |
| 3 (2213-54-1) | 196 | $17 \times 10^{-9}$ | $1.03 \times 10^{-5}$ | 21 |
| 4 (2213-56-2) | 139 | $17 \times 10^{-9}$ | $1.38 \times 10^{-5}$ | 19 |
| 5 (2151-57) | 138 | $7.8 \times 10^{-9}$ | $1.42 \times 10^{-5}$ | 22 |
| 6 | — | — | — | — |
| 7 (2151-58) | 186 | $3.7 \times 10^{-9}$ | $1.32 \times 10^{-5}$ | 17 |
| 8 (2213-47-2) | 167 | $2.3 \times 10^{-9}$ | $0.95 \times 10^{-5}$ | 14 |
| 9 (2213-54-2) | 180 | — | — | 30 |
| 10 (2213-56-1) | 145 | $18 \times 10^{-9}$ | $1.73 \times 10^{-5}$ | 27 |
| 11 (2213-59-2) | 185 | — | — | 3 |

The invention claimed is:

1. An amperometric analyte sensor apparatus comprising:
a base layer comprising a working electrode;
an analyte sensing layer coating the working electrode; and
an analyte modulating layer coating the analyte sensing layer, wherein:
the analyte modulating layer comprises a blended mixture of a linear polyurethane/polyurea polymer and a branched acrylate polymer;
the linear polyurethane/polyurea polymer exhibits a permeability to glucose that decreases by between 1% and 8% per degree centigrade as temperature is increased from 22 to 40 degrees centigrade;
the branched acrylate polymer exhibits a permeability to glucose that increases by between 1% and 8% per degree centigrade as temperature is increased from 22 to 40 degrees centigrade;
the linear polyurethane/polyurea polymer and the branched acrylate polymer are blended at a ratio of between 1:1 and 1:20 by weight %; and
the analyte modulating layer comprises a blend of:
(1) a polyurethane/polyurea polymer formed from a mixture comprising:
(a) a diisocyanate;
(b) a hydrophilic polymer comprising a hydrophilic diol or hydrophilic diamine; and
(c) a siloxane having an amino, hydroxyl or carboxylic acid functional group at a terminus; and
(2) a branched acrylate polymer formed from a mixture comprising:
(a) a butyl, propyl, ethyl or methyl-acrylate;
(b) an amino-acrylate;
(c) a siloxane-acrylate; and
(d) a poly(ethylene oxide)-acrylate.

2. The analyte sensor apparatus of claim 1, wherein the blended analyte modulating layer exhibits a permeability to glucose that changes less than 2% per degree centigrade over a temperature range of 22 to 40 degrees centigrade.

3. The analyte sensor apparatus of claim 1, wherein the analyte modulating layer facilitates in vivo hydration of the sensor so that levels of an in vivo analyte can be sensed less than 45 minutes after sensor implantation into an in vivo environment.

4. The analyte sensor apparatus of claim 1, wherein the sensor does not include a separate layer of an adhesion promoting material disposed between the analyte sensing layer and the analyte modulating layer.

5. The analyte sensor apparatus of claim 1, further comprising at least one of:
a protein layer coating the analyte sensing layer; or
a cover layer coating the analyte sensor apparatus, wherein the cover layer comprises an aperture positioned on the cover layer so as to facilitate an analyte present in an in vivo environment from contacting and diffusing through an analyte modulating layer; and contacting the analyte sensing layer.

6. The analyte sensor apparatus of claim 1, wherein the analyte sensing layer comprises glucose oxidase.

7. The analyte sensor apparatus of claim 1, wherein the base layer comprises a plurality of electrodes including the working electrode, a counter electrode and a reference electrode.

8. The analyte sensor of claim 7, wherein the base layer comprises a plurality of working electrodes, counter electrodes and reference electrodes.

9. The analyte sensor of claim 1, wherein a pulsed voltage is used to obtain a signal from an electrode.

10. The analyte sensor apparatus of claim 1 wherein the branched acrylate polymer is formed from a reaction mixture further comprising a hydroxyl-acrylate.

11. The analyte sensor of claim 1, wherein the analyte modulating layer comprises a blend of:
 (1) a polyurethane/polyurea polymer formed from a mixture comprising:
  (a) a diisocyanate;
  (b) a hydrophilic polymer comprising a hydrophilic diol or hydrophilic diamine; and
  (c) a siloxane having an amino, hydroxyl or carboxylic acid functional group at a terminus; and
 (2) a branched acrylate polymer formed from a mixture comprising:
  (a) a methyl methacrylate;
  (b) a 2-(dimethylamino)ethyl methacrylate;
  (c) a polydimethyl siloxane monomethacryloxypropyl;
  (d) a poly(ethylene oxide) methyl ether methacrylate; and
  (e) a 2-hydroxyethyl methacrylate.

12. A method of making an analyte sensor apparatus for implantation within a mammal comprising the steps of:
 providing a base layer;
 forming a working electrode on the base layer;
 forming an analyte sensing layer on the conductive layer, wherein the analyte sensing layer includes an oxidoreductase;
 forming an analyte modulating layer on the analyte sensing layer, wherein:
 the analyte modulating layer comprises a blended mixture of:
 (1) a first polymer formed from a mixture comprising:
  (a) a diisocyanate;
  (b) at least one hydrophilic diol or hydrophilic diamine; and
  (c) a siloxane; and
 (2) a second polymer formed from a mixture comprising:
  (a) a 2-(dimethylamino) ethyl methacrylate;
  (b) a methyl methacrylate;
  (c) a polydimethyl siloxane monomethacryloxypropyl; and
  (d) a poly(ethylene oxide) methyl ether methacrylate; and
 the first polymer and the second polymer are blended at a ratio of between 1:1 and 1:20 by weight %; and
 forming a cover layer on the analyte modulating layer.

13. The method of claim 12, wherein the analyte modulating layer exhibits a permeability to glucose that changes less than 2% per degree centigrade over a temperature range of 21 to 40 degrees centigrade.

14. The method of claim 12, wherein the second polymer is formed from a reaction mixture further comprising a 2-hydroxyethyl methacrylate.

15. The method of claim 12, wherein the analyte modulating layer is formed to exhibit adhesive properties that allow the analyte modulating layer composition to adhere to adjacent layers in the analyte sensing apparatus so that the analyte sensor apparatus does not include an adhesion promoting layer disposed between the analyte sensing layer and an adjacent layer.

16. An amperometric analyte sensor apparatus comprising:
 a base layer comprising a working electrode;
 an analyte sensing layer coating the working electrode; and
 an analyte modulating layer coating the analyte sensing layer, wherein the analyte modulating layer comprises a blend of:
 (1) a polyurethane/polyurea polymer formed from a mixture comprising:
  (a) a diisocyanate;
  (b) a hydrophilic polymer comprising a hydrophilic diol or hydrophilic diamine; and
  (c) a siloxane having an amino, hydroxyl or carboxylic acid functional group at a terminus; and
 (2) a branched acrylate polymer formed from a mixture comprising:
  (a) a butyl, propyl, ethyl or methyl-acrylate;
  (b) an amino-acrylate;
  (c) a siloxane-acrylate; and
  (d) a poly(ethylene oxide)-acrylate; and
 the polyurethane/polyurea polymer and the branched acrylate polymer are blended at a ratio of between 1:1 and 1:20 by weight %.

* * * * *